(12) United States Patent
Jaasma et al.

(10) Patent No.: US 11,672,981 B2
(45) Date of Patent: Jun. 13, 2023

(54) METHODS AND DEVICES FOR TREATING AND MANAGING ADDICTION

(71) Applicant: TheraNova, LLC, San Francisco, CA (US)

(72) Inventors: Michael Jaasma, San Francisco, CA (US); Michael Hemati, San Francisco, CA (US); Daniel R. Burnett, San Francisco, CA (US)

(73) Assignee: TheraNova, LLC, San Francisco, CA (US)

( * ) Notice: Subject to any disclaimer, the term of this patent is extended or adjusted under 35 U.S.C. 154(b) by 194 days.

(21) Appl. No.: 16/823,767

(22) Filed: Mar. 19, 2020

(65) Prior Publication Data

US 2020/0215325 A1 Jul. 9, 2020

Related U.S. Application Data

(63) Continuation of application No. PCT/US2018/052028, filed on Sep. 20, 2018.

(60) Provisional application No. 62/591,661, filed on Nov. 28, 2017, provisional application No. 62/561,992, filed on Sep. 22, 2017.

(51) Int. Cl.
| | |
|---|---|
| *A61N 1/36* | (2006.01) |
| *A61B 5/02* | (2006.01) |
| *A61B 5/0531* | (2021.01) |
| *A61B 5/11* | (2006.01) |
| *A61B 5/00* | (2006.01) |

(52) U.S. Cl.
CPC ..... *A61N 1/36028* (2013.01); *A61N 1/36031* (2017.08); *A61N 1/36034* (2017.08); *A61B 5/02* (2013.01); *A61B 5/0531* (2013.01); *A61B 5/1101* (2013.01); *A61B 5/4266* (2013.01); *A61B 2562/0219* (2013.01)

(58) Field of Classification Search
CPC ........ A61B 5/02; A61N 1/36; A61N 1/36028; A61N 1/36031
See application file for complete search history.

(56) References Cited

U.S. PATENT DOCUMENTS

| | | | |
|---|---|---|---|
| 5,578,645 A | 11/1996 | Askanazi et al. | |
| 7,734,340 B2* | 6/2010 | De Ridder | A61N 1/36117 607/2 |
| 8,700,163 B2* | 4/2014 | Terry, Jr. | A61N 1/36014 607/45 |

(Continued)

FOREIGN PATENT DOCUMENTS

| | | |
|---|---|---|
| WO | WO 2017/044967 | 3/2017 |
| WO | WO 2019/060598 | 3/2019 |

*Primary Examiner* — Deborah L Malamud
(74) *Attorney, Agent, or Firm* — Levine Bagade Han LLP

(57) ABSTRACT

Methods and devices for treating and managing addiction are disclosed where an apparatus for mitigating addictive behavior may generally comprise at least two electrodes for positioning in proximity to an ulnar nerve of a body of a subject and one or more sensors configured to detect physiologic parameters which correlate to one or more symptoms indicative of addictive behavior of the subject. A pulse generator may be programmed to receive a sensor output based on the detected physiologic parameters and to apply a treatment stimulation to the ulnar nerve through a skin surface of the subject such that the addictive behavior of the subject is reduced.

52 Claims, 19 Drawing Sheets

(56) References Cited

U.S. PATENT DOCUMENTS

| | | |
|---|---|---|
| 2002/0177232 A1 | 11/2002 | Melker et al. |
| 2006/0095088 A1 | 5/2006 | De Ridder |
| 2006/0200208 A1 | 9/2006 | Terry et al. |
| 2011/0152974 A1 | 6/2011 | Rezai et al. |
| 2015/0031964 A1 | 1/2015 | Bly et al. |
| 2017/0157398 A1 | 6/2017 | Wong et al. |
| 2017/0266443 A1 | 9/2017 | Rajguru et al. |

* cited by examiner

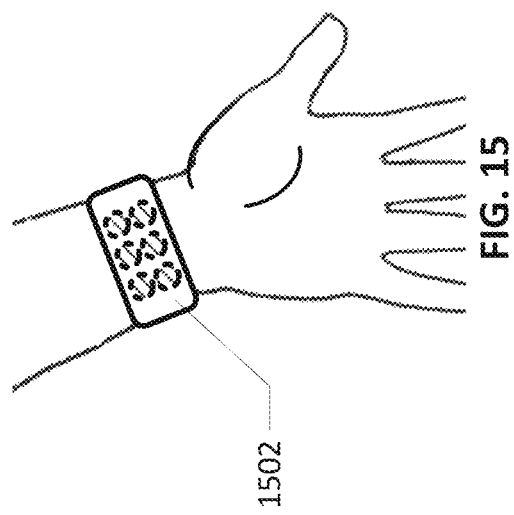
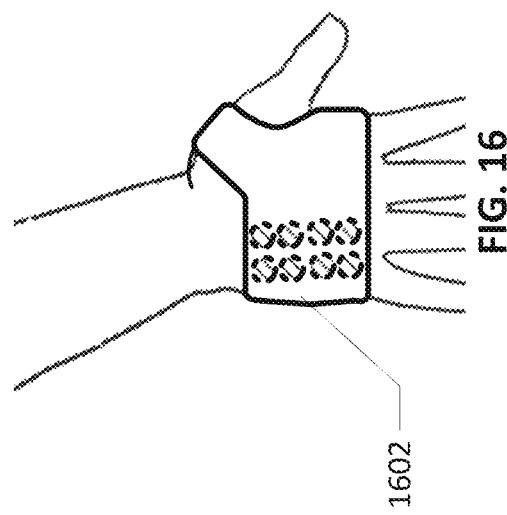
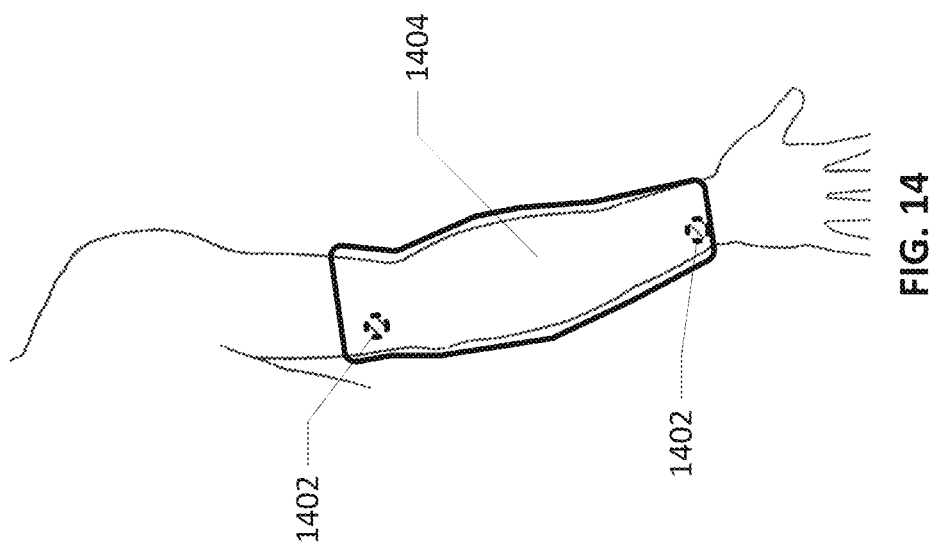

2002

2104
2102

1902
1902
1904

Schematic Representation of Output (one 10 pulse period)

METHODS AND DEVICES FOR TREATING AND MANAGING ADDICTION

CROSS-REFERENCE TO RELATED APPLICATIONS

This application is a continuation of International Application No. PCT/US2018/052028 filed Sep. 20, 2018, which claims the benefit of priority to U.S. Provisional Application No. 62/561,992 filed Sep. 22, 2017 and U.S. Provisional Application No. 62/591,661 filed Nov. 28, 2017, each of which is incorporated herein by reference in its entirety.

The following applications are also incorporated herein by reference in their entirety for all purposes: PCT Application Serial No. PCT/US10/54167 filed Oct. 26, 2010; PCT Application Serial No. PCT/US10/054353 filed Oct. 27, 2010; U.S. patent application Ser. No. 12/508,529 filed Jul. 23, 2009, which is a continuation in part of U.S. patent application Ser. No. 11/866,329 filed Oct. 2, 2007, which claims priority to U.S. Provisional Patent Application Ser. No. 60/848,720 filed Oct. 2, 2006; U.S. patent application Ser. No. 12/695,087 filed Jan. 27, 2010, which is a continuation of U.S. patent application Ser. No. 11/332,797 filed Jan. 17, 2006; U.S. patent application Ser. No. 12/509,362 filed Jul. 24, 2009; Ser. No. 12/469,365 filed May 20, 2009 which is a continuation of U.S. patent application Ser. No. 11/866,329 filed Oct. 2, 2007 which claims priority to U.S. Provisional Patent Application Ser. No. 60/848,720 filed Oct. 2, 2006, and Ser. No. 12/469,625 filed May 20, 2009 which is a continuation of U.S. patent application Ser. No. 11/866,329 filed Oct. 2, 2007 which claims priority to U.S. Provisional Patent Application Ser. No. 60/848,720 filed Oct. 2, 2006; and Ser. No. 12/509,304 filed Jul. 24, 2009 which is a continuation of U.S. patent application Ser. No. 12/508,529 filed Jul. 23, 2009 which is a continuation-in-part of U.S. patent application Ser. No. 11/866,329 filed Oct. 2, 2007 which claims priority to U.S. Provisional Patent Application Ser. No. 60/848,720 filed Oct. 2, 2006; and Ser. No. 12/509,345 filed Jul. 24, 2009 which is a continuation of U.S. patent application Ser. No. 12/508,529 filed Jul. 23, 2009 which is a continuation-in-part of U.S. patent application Ser. No. 11/866,329 filed Oct. 2, 2007 which claims priority to U.S. Provisional Patent Application Ser. No. 60/848,720 filed Oct. 2, 2006.

FIELD OF THE INVENTION

The present apparatus and methods relate generally to energy emitting apparatus and methods for providing a medical therapy. The apparatus and methods may provide for nerve and other tissue modulation or stimulation therapies, including stimulation of acupuncture points and/or lines.

BACKGROUND OF THE INVENTION

Treatment for substance abuse and addiction has been tried with therapy, drugs and acupuncture. Although some success has been achieved using acupuncture, it has not been generally reproducible or consistent.

The use of pulsed, or non-pulsed electrical stimulation therapy, using electrodes which are implanted, percutaneous or transcutaneous, has been used as a therapy in a variety of medical applications, including muscle and nerve stimulation applications, however, it has not been applied specifically to the treatment of addiction and addiction withdrawal symptoms.

SUMMARY OF THE INVENTION

Disclosed herein are devices and methods for treating addiction and/or substance abuse in subjects using electrical nerve stimulation. In some embodiments, the ulnar nerve, or a branch of the ulnar nerve, is stimulated. In some embodiments, an afferent nerve fiber is stimulated. In some embodiments, an efferent nerve fiber is stimulated. In some embodiments, the Heart Meridian acupuncture line is stimulated. In some embodiments, feedback is collected by a controller to determine the effectiveness of the stimulation. In some embodiments, feedback is collected in the form of measuring M-waves or F-waves. In some embodiments, the electrical nerve stimulation is transcutaneous. In some embodiments, the electrical nerve stimulation is percutaneous. In some embodiments, the electrical nerve stimulation is via implanted electrodes. In some embodiments, the device for stimulating (and possibly for monitoring the feedback relating to the stimulation) consists of a portable and/or wearable device. In some embodiments, the device is used frequently throughout the day. In some embodiments, the device is used once/day or less, and may not be wearable.

In some embodiments of the treatment device, treatment efficacy is sensed using nerve sensory sensing or motor sensory sensing.

A method of using the treatment device may include positioning a stimulator electrode on the skin near the ulnar nerve, or a branch of the ulnar nerve. Electrical stimulation may be delivered through or across the skin surface to the target nerve to stimulate the target nerve, while remaining safe and tolerable to the patient. The skin surface may be a glabrous skin surface, such as a palm of a hand, or may be another skin surface.

A method of using the treatment device may include positioning a stimulator electrode on the skin near the Heart Meridian acupuncture line, or points. Electrical stimulation may be delivered through or across the skin surface to the target points and/or line to stimulate the target points and/or line, while remaining safe and tolerable to the patient. The skin surface may be a glabrous skin surface, such as a palm of a hand, or may be another skin surface.

In certain variations, a device, e.g., an ergonomic device, for providing transdermal electrical stimulation therapy to a patient is provided. The device may be configured to position a stimulator electrode over a skin surface of the subject to deliver transdermal electrical stimulation through or across the skin surface to an underlying target nerve, resulting in stimulation of the target nerve. In some embodiments, one or more electrodes may be gel electrodes.

In certain variations, a method for providing an energy based stimulation therapy to a subject is provided. The method may include positioning an energy emitting device in proximity to a skin surface overlying a target tissue, line and/or point. Energy may be delivered through the skin surface to the target tissue to stimulate the target tissue line and/or point.

In certain variations, another method for providing an energy based stimulation therapy to a subject is proved. The method may include positioning an energy emitting device in proximity to a skin surface overlying a target nerve, line and/or point. Energy may be delivered at a frequency of about 1 Hz to about 30 Hz through the skin surface to the target, thereby generating motor and/or sensory nerve conduction of a target nerve while remaining safe and tolerable to the subject. Optionally, energy may be delivered at less than 10 Hz to generate nerve conduction. Optionally, energy may be delivered at about 2 Hz. Optionally, energy may be delivered at about 100 Hz.

In certain variations, One or more sensors may be utilized to detect electrical conduction in a target nerve, to detect a muscular response caused by an electrical conduction in the target nerve, or to detect stimulation of a nerve, muscle or other body tissues and to provide feedback about the efficacy of the applied stimulation therapy. A controller in communication with the sensor may be adjustable to vary a current through the at least one electrode so as to adjust the stimulation strength and/or frequency and/or duration of the target nerve, muscle, line, point or other body tissues. Optionally, a user or patient may detect stimulation of a nerve, muscle or body tissue and the therapy may be adjusted based on feedback from the user or patient.

In certain variations, the controller may be configured to intermittently apply or deliver stimulation to a target nerve, muscle or tissue without causing habituation of the target nerve, muscle or tissue.

In some embodiments, the controller may be configured to apply stimulation based on a preprogrammed pattern of frequencies, durations, intensities, etc.

In certain variations, methods of stimulation therapy may include one or more of the following steps. A first portion of a patient's body may be positioned relative to or in proximity to an electrode or an electrode may be positioned relative to or in proximity to a first portion of a patient's body, such that a target nerve, muscle or tissue within the first portion of the body is in proximity to one or more electrodes disposed within or along the device. A current may be passed through the electrode near the target nerve, muscle or tissue. A second electrode may be included in the device to serve as a ground electrode. An electrical conduction through the target nerve, a muscular response caused by an electrical conduction through the target nerve or stimulation of a nerve, muscle, or body tissue may be detected by a sensor positioned along a second portion of the body. A signal from the sensor indicative of the electrical conduction or stimulation may be received by the controller, which may provide feedback about the efficacy of the applied electrical stimulation therapy. The current parameters (frequency, duration, intensity, etc.) may be adjusted by a controller in communication with the electrodes based on the feedback, or the subject may be alerted to adjust parameters, including the fit of the device, manually.

Optionally, a user may detect stimulation of a nerve, muscle or body tissue and the therapy may be adjusted based on feedback from the user. In certain variations, pulsed electrical energy may be intermittently applied or delivered a target nerve, muscle or tissue without causing habituation of the target nerve, muscle or tissue. Such intermittent stimulation may be used to treat chronic conditions without causing habituation.

In certain variations, applicators may be ergonomic or may be designed or configured to accommodate, approximate or be positioned relative to or in proximity to specific regions of the body or anatomy. The specific regions of the body or anatomy may be positioned relative to the applicators, or the applicators may be positioned relative to the specific regions of the body or anatomy.

In one embodiment, the invention provides a method or device for providing transdermal electrical stimulation therapy to a subject including positioning a stimulator electrode over a skin surface overlying the ulnar nerve, or a branch of the ulnar nerve, and/or the Heart Meridian acupuncture line/points of the subject and delivering electrical stimulation via a pulse generator transdermally through the skin surface and to the ulnar nerve and/or the Heart Meridian line/points to stimulate the ulnar nerve or tissue so that addiction withdrawal symptoms or addiction symptoms experienced by the subject are mitigated. The pulses generated during the electrical stimulation therapy may include pulses of one or two or more different magnitudes, frequencies and/or durations. For example, use of the device may decrease the user's use of an addictive substance, such as tobacco, nicotine, opioids, pain medication, other medications, sleep aids, illicit drugs, *cannabis*, cocaine, food, alcohol, etc. Use of the device may be used to decrease the user's participation in an addictive activity, such as gambling, phone usage, electronics usage, etc.

In one embodiment, the invention provides a method or device for providing percutaneous electrical stimulation therapy to a subject including positioning a stimulator electrode through a skin surface overlying the ulnar nerve, or a branch of the ulnar nerve, and/or the Heart Meridian acupuncture line/points of the subject and delivering electrical stimulation via a pulse generator percutaneously through the skin surface and to the ulnar nerve and/or the Heart Meridian line/points to stimulate the ulnar nerve or tissue so that addiction withdrawal symptoms or addiction symptoms experienced by the subject are mitigated. The pulses generated during the electrical stimulation therapy may include pulses of one or two or more different magnitudes, frequencies and/or durations.

Withdrawal/addiction symptoms may include:
Cravings/temptations
Shakiness
Irritability
Increased sensitivity to pain
Emotional instability
Anxiety
Depression
Restlessness
Insomnia
Sweating
Hot flashes
Flu-like symptoms
Weakness
Body aches/headaches
Lack of appetite
Increased appetite
Use of addictive substance (relapse)
Participating in addictive activity
Phone or electronic device overuse
Unacceptable level of use of an addictive substance
Unacceptable level of participation in an addictive activity
Use of other harmful substance
Use of methadone
Death
Tremors
Tension
Panic attacks
Difficulty concentrating
Short-term memory loss
Heart palpitations
Nausea
Vomiting
Muscle pain and stiffness
Hypertension
Irregular heart rate
Fatigue
Clammy skin Dizziness Mood swings Nightmares Elevated heart rate Loss of color in the face Dehydration Shallow breathing In some embodiments, the electrical stimulation is delivered at a frequency of about 5 Hz to about 60 Hz. In some embodiments, the frequency is adjustable and may range from about 2 Hz to about 100 Hz. In some embodiments, the stimulation is delivered at alternating frequencies of about 2 Hz and about 100 Hz. In some embodiments, the stimulator electrode is a surface electrode. The electrical stimulation may be delivered intermittently or on a chronic basis.

In some embodiments, the device includes a sensor (which may be a surface electrode, or other type of electrode) for detecting nerve stimulation which receives a signal from the sensor indicative of the detected electrical stimulation thereby providing a feedback about the efficacy of the applied electrical stimulation therapy. In some embodiments, the therapy is adjusted or optimized as a result of the sensed feedback. An M-wave and/or F-wave may be detected by the sensor. A parameter of the M-wave and/or F-wave may be displayed to the subject.

In some embodiments, the feedback is queried by a controller such that the electrical stimulation therapy is adjusted to ensure that a minimum amount of energy is being applied to stimulate the target while reducing the risk of burns or intolerance. Alternatively, the feedback may be queried such that the positioning of the stimulator electrode is adjusted to optimize the electrical stimulation therapy.

In some embodiments, a return, or ground, electrode may be positioned on the subject to facilitate penetration of an electrical current to stimulate the target. The stimulator electrode may be attached to the skin surface with an adhesive. The stimulator electrode may be positioned over the skin surface with an ergonomic applicator.

In some embodiments, the electrical stimulation is automatically paused for a preset amount of time every 10 minutes to overcome habituation. In some embodiments, the electrical stimulation is automatically paused for a preset amount of time every 10 minutes based on feedback provided by a sensor regarding target stimulation or habituation.

In some embodiments, once tetany is detected in a patient, indicating that a threshold frequency of the applied stimulation has been reached, the strength of the applied stimulation is automatically or manually decreased.

In some embodiments, electrical stimulation is provided by delivering a cycle comprising a preset number of pulses followed by a pause in stimulation, followed by a preset number of pulses, and repeating the cycle as necessary.

In some embodiments, the device is used to treat addiction withdrawal symptoms.

In some embodiments, the device is used to treat Schizophrenia or other related mental disorders.

In some embodiments, the device is used to treat Post Traumatic Stress Disorder, or PTSD.

In some embodiments, the device is used to treat eating disorders.

In some embodiments, the device is used to treat depression.

In one variation, an apparatus for mitigating addictive behavior may generally comprise at least two electrodes for positioning in proximity to an ulnar nerve of a body of a subject and one or more sensors configured to detect physiologic parameters which correlate to one or more symptoms indicative of addictive behavior of the subject. A pulse generator may be programmed to receive a sensor output based on the detected physiologic parameters and to apply a treatment stimulation to the ulnar nerve through a skin surface of the subject such that the addictive behavior of the subject is reduced. The pulse generator may be configured to generate pulses of one or more different magnitudes, frequencies and/or durations.

In another variation, an apparatus for mitigating addictive behavior may generally comprise at least two electrodes for positioning in proximity to an ulnar nerve of a body of a subject and one or more sensors configured to detect physiologic parameters which correlate to one or more symptoms indicative of withdrawal from an addictive behavior of the subject. A pulse generator may be programmed to receive a sensor output based on the detected physiologic parameters and to apply a treatment stimulation to the ulnar nerve through a skin surface of the subject such that the addictive behavior of the subject is reduced. The pulse generator may be configured to generate pulses of one or more different magnitudes, frequencies and/or durations.

In one variation for a method for mitigating addictive behavior, the method may generally comprise detecting one or more physiologic parameters via one or more sensors correlating to one or more symptoms indicative of withdrawal from an addictive behavior of a subject, determining a treatment stimulation based on the sensor output from the detected physiologic parameters, and applying the treatment stimulation via at least two electrodes to an ulnar nerve through a skin surface of the subject via a pulse generator such that the addictive behavior of the subject is reduced. The pulse generator may be configured to generate pulses of one or more different magnitudes, frequencies and/or durations.

Other features and advantages will appear hereinafter. The features and elements described herein can be used separately or together, or in various combinations of one or more of them.

BRIEF DESCRIPTION OF THE DRAWINGS

The drawings constitute a part of this specification and include exemplary embodiments of the invention, which may be embodied in various forms. It is to be understood that in some instances various aspects of the embodiments may be shown exaggerated or enlarged to facilitate an understanding of the embodiments.

FIG. 14 shows electrodes incorporated into a sleeve.

FIG. 15 shows electrodes incorporated into a wristband.

FIG. 16 shows electrodes incorporated into hand-band, glove, or fingerless glove.

DETAILED DESCRIPTION OF THE INVENTION

Figure 1:
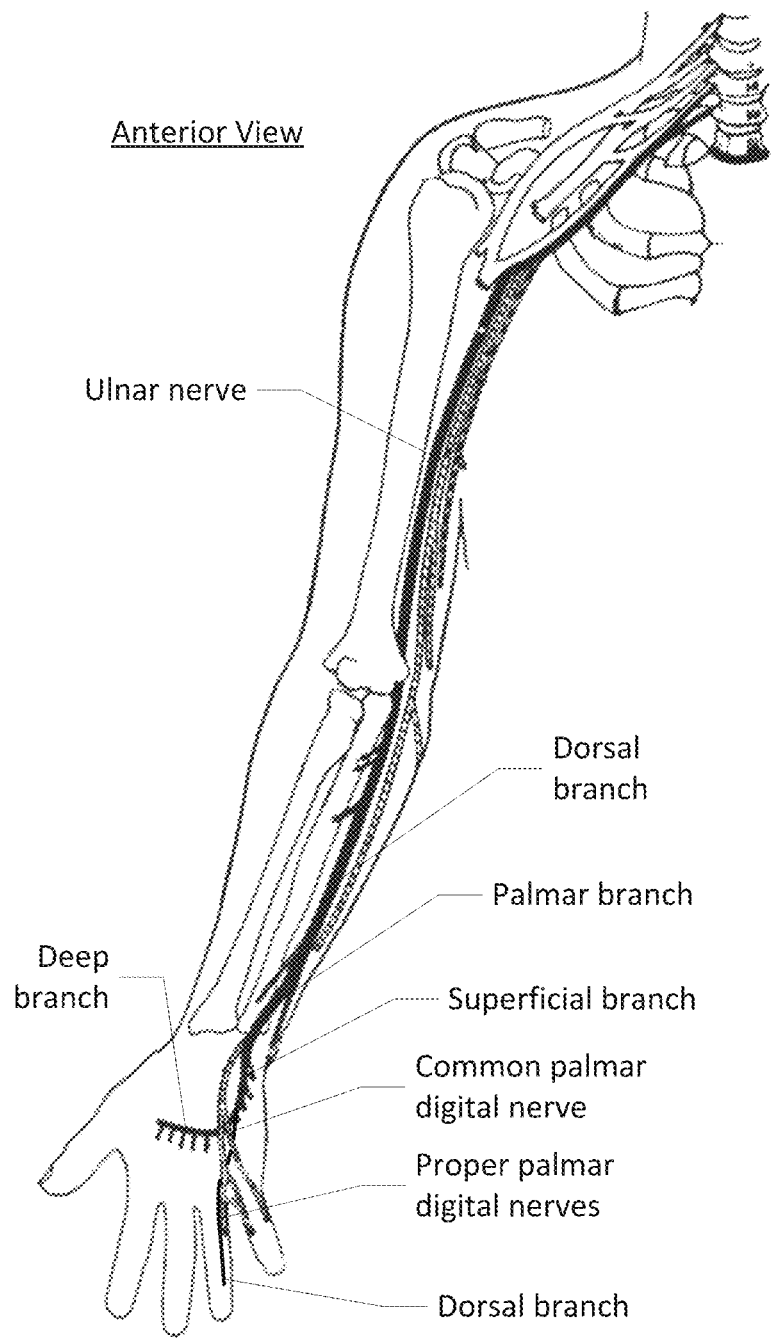
FIG. 1 shows the anterior or palmar view of the forearm and the Ulnar nerve.

In certain variations, various apparatus and methods for providing electrical stimulation therapy are provided. In certain variations, various apparatus and methods may provide for nerve and other tissue modulation or stimulation therapies, including both excitation and blocking of nerve impulses. In certain variations, a low frequency induction therapy may be performed. In certain variations, a high frequency induction therapy may be performed. In certain variations, these apparatus and methods may be useful in the treatment and prevention of addiction and/or withdrawal symptoms, and other conditions.

In certain variations, an energy emitting apparatus for delivering a medical therapy that includes one or more energy generators, a logic controller electrically connected to the one or more energy generators, and one or more sensors for detecting electric conduction in a target nerve, which are connected to the logic controller is provided. The one or more energy generators produce energy focused on the target nerve upon receiving a signal from the logic controller, and the applied energy is varied by the logic controller according to an input provided by the one or more sensors based on electric conduction in the target nerve. The feedback provided by the sensors to the logic controller about the efficacy of the applied treatment may cause the logic controller to modulate the current transmitted to the electrodes, including frequency, location, duration, amplitude, pause periods etc.

In yet other variations, the source of energy for nerve stimulation may be electrical energy and nerve conduction may be detected at a site sufficiently distant from the site of stimulation, so to enable detection of nerve conduction despite any interference from the direct electrical stimuli. In these variations, direct electrical stimulation of nerve and muscle may be tailored to provide optimal therapy and, in the case of electrode migration or other electrode malfunction, to report lack of stimulation of the bodily tissues. Furthermore, these variations enable a reduction in power requirement, because control of the signal is provided by the sensor to the signal generator loop.

Optionally, the variations disclosed herein may incorporate an electrode needle. Optionally, the variations or systems disclosed herein may be utilized without a sensor or mechanism for detecting conduction or stimulation.

Methods of use of the above apparatus, systems and variations thereof for treating various conditions are also described herein.

In certain variations, treatment of a patient using electrical stimulation may be monitored and/or adjusted based on the detection of feedback signals using primarily F-wave detection or based on the detection of F-waves or M-waves. For example, detection of an F-wave or F-wave feedback (e.g., via a sensor or electrode sensor) may be used in monitoring and/or to adjust the applied stimulation therapy. Optionally, stimulation may be ramped up until an F-wave is detected and then adjusted as necessary. F-wave detection measures nerve conduction velocity. F-wave detection may be used as opposed to H-reflex detection, which measures reflectory reaction from muscles. In other variations, optionally both F-wave and H-reflex detection may be used or solely H-reflex detection may be used. Stimulating to a sub-motor stimulation may be performed. In certain variations, F-waves, M-waves and/or H-reflex may be detected in the foot, hand or other body part.

Electrical energy may be applied or delivered using any of the devices, applicators or electrodes described herein at specified frequencies and/or parameters or using various duty cycles. In one example, electrical energy may be applied at a frequency of 5 Hz to 20 Hz (e.g., to provide supermaximal stimulation) in a train of 5 pulses followed by a ¼ second break, and then another train of 5 pulses. Up to 10 pulses per treatment cycle may be provided. The train of 10 pulses can be repeated as needed. In another example, a train of 10 pulses followed by a break and then another 10 pulses may applied, e.g., at a frequency of 5 Hz to 20 Hz or at about 20 Hz. The ¼ second break time may be varied as well as the number of pulses applied and the number of cycles. This pulsed treatment may be applied through one or more or several cycles. The pulsed treatment or stimulation may produce F-waves which may be detected. In certain variations, any of the treatment parameters as described herein may be applied where only half of the pulses are stimulatory, e.g., one or more cycles of pulses may be provided at 20 Hz, where only half of the pulses are stimulatory.

In other variations, the treatment parameters may vary, e.g., stimulation frequency may be applied for an interval ranging from 0 to 100 minutes or greater or as necessary to treat symptoms followed by a varying frequency for a time interval. In certain variations, for example, stimulation at certain frequency may be applied or provided for varying times with total stimulation of 15, 20, 30, 40, 50 or 60 minutes. In certain variations, for example, the change in stimulation frequency may be for an interval ranging from 0 to 100 seconds, or 5 to 60 seconds or 20 to 40 seconds.

Certain frequencies, e.g., frequencies applied at greater than 20 Hz, may lead to a painful condition called tetany (i.e., painful, involuntary muscle cramping), which is an indication that the upper level for frequency has been reached in the patient. Tetany may be monitored using a sensor, e.g., an EMG sensor or Electromyography, to provide feedback regarding tetany. Tetany may be distinguished by EMG. Once the system detects the beginning of tetany or provides tetany feedback, the treatment frequency or power (of the stimulation delivered by an electrode or device) may be reduced, adjusted or halted automatically or manually. The frequency at which tetany is experienced may vary in different individuals.

The addiction treatment system may use electrical stimulation of one or more of the Ulnar nerve, the Median nerve, or other nerves, either alone or simultaneously, separately or with other types of therapy to treat addiction and/or addiction withdrawal symptoms. In some embodiments, treatment can be combined with certain drugs to increase treatment effectiveness.

In some embodiments, electrical stimulation of one or more acupuncture lines and/or points, including the HT (heart meridian) line/points, either alone or simultaneously, separately or with stimulation of the Ulnar nerve may be used to treat addiction and/or addiction withdrawal symptoms.

Devices used to stimulate one or more of the Ulnar nerve and/or the HT line can be a completely external device, a fully implantable device or a device that comprises both external and internal components. The devices typically comprise a pulse generating component that provides an electrical wave form as output. The electrical pulse comprises certain typical parameters, such as pulse width, frequency, number of pulses and amplitude among other parameters. The choice of parameters may depend on the nerve, the location of the electrodes, the desired effect sought and the amount of time the therapy treatment occurs.

Figure 2:
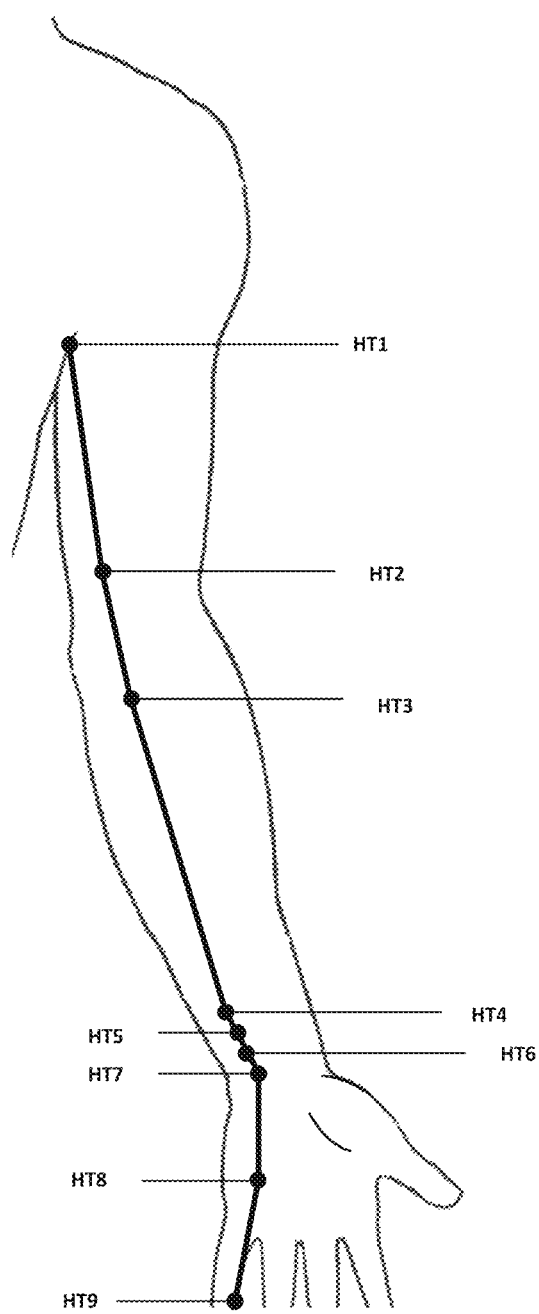
FIG. 2 shows the anterior or palmer view of the forearm and the HT acupuncture line and points.
Figure 3:
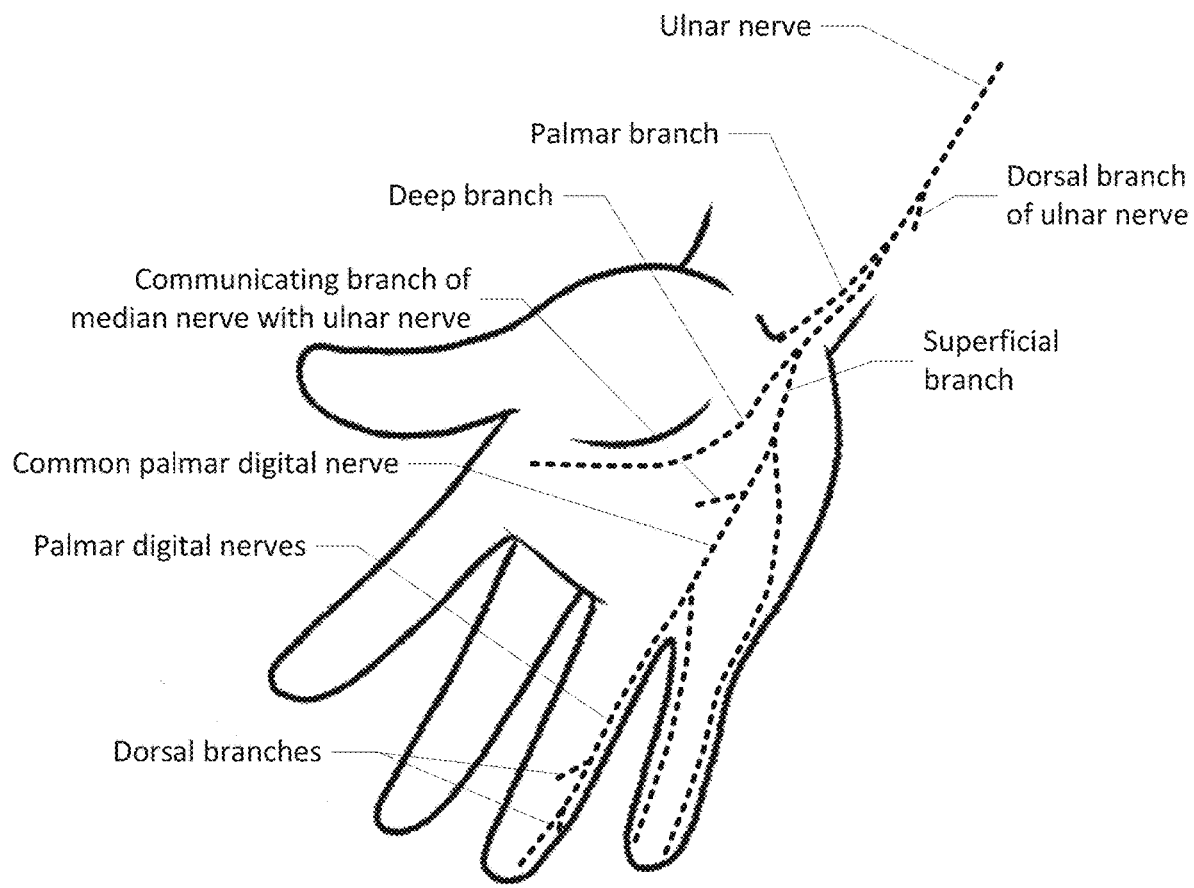
FIG. 3 shows a close up view of the Ulnar nerve and its branches.
Figures 4A, 4B:
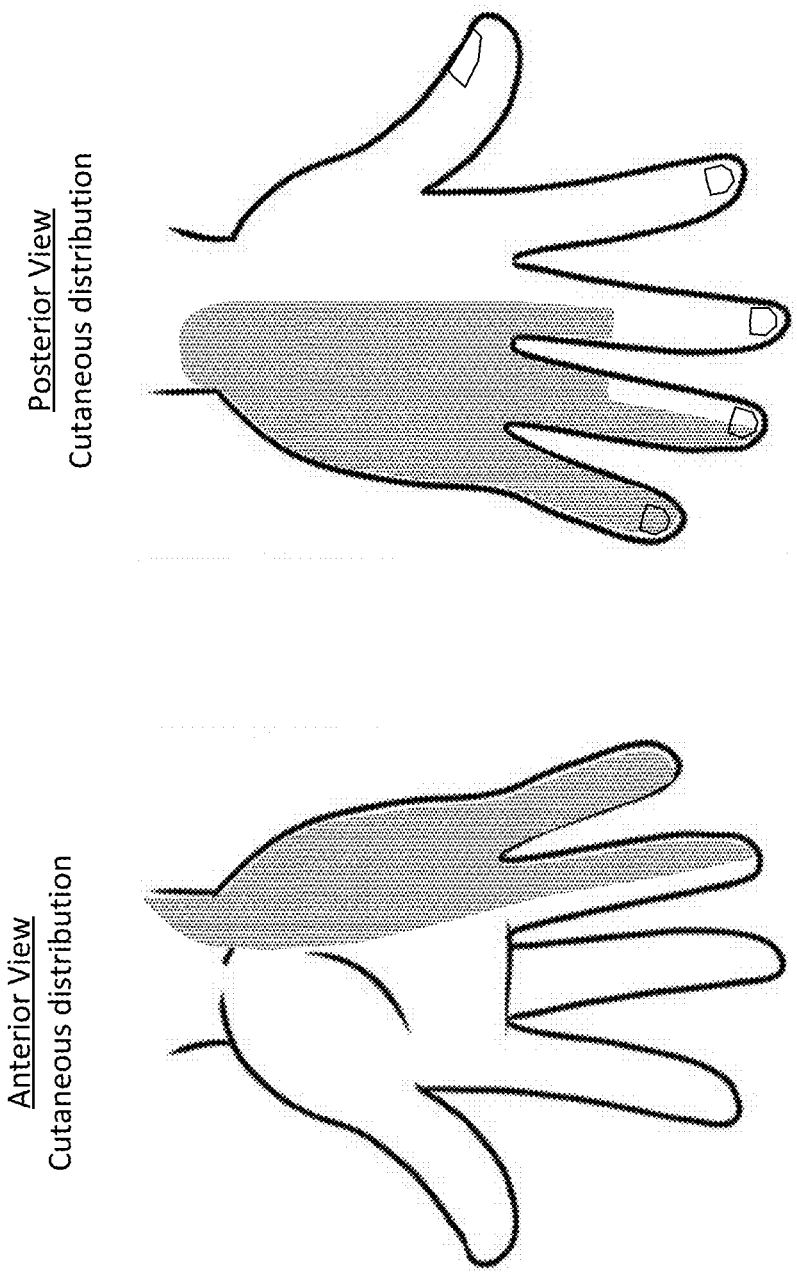
FIG. 4A shows the anterior view of the cutaneous distribution of the Ulnar nerve.
FIG. 4B shows the posterior view of the cutaneous distribution of the Ulnar nerve.

One method of using the addiction treatment system is to stimulate one or both of the Ulnar nerve (or a branch thereof) and the HT acupuncture line to treat addiction withdrawal symptoms. The Ulnar nerve innervate portions of the arm and hands. FIG. 1 shows the anterior or palmar view of the forearm and the Ulnar nerve. FIG. 2 shows the anterior or palmer view of the forearm and the HT acupuncture line and points. FIG. 4A shows the anterior view of the cutaneous distribution of the Ulnar nerve. FIG. 4B shows the posterior view of the cutaneous distribution of the Ulnar nerve. FIG. 3 shows a close up view of the Ulnar nerve and its branches.

Figure 5:
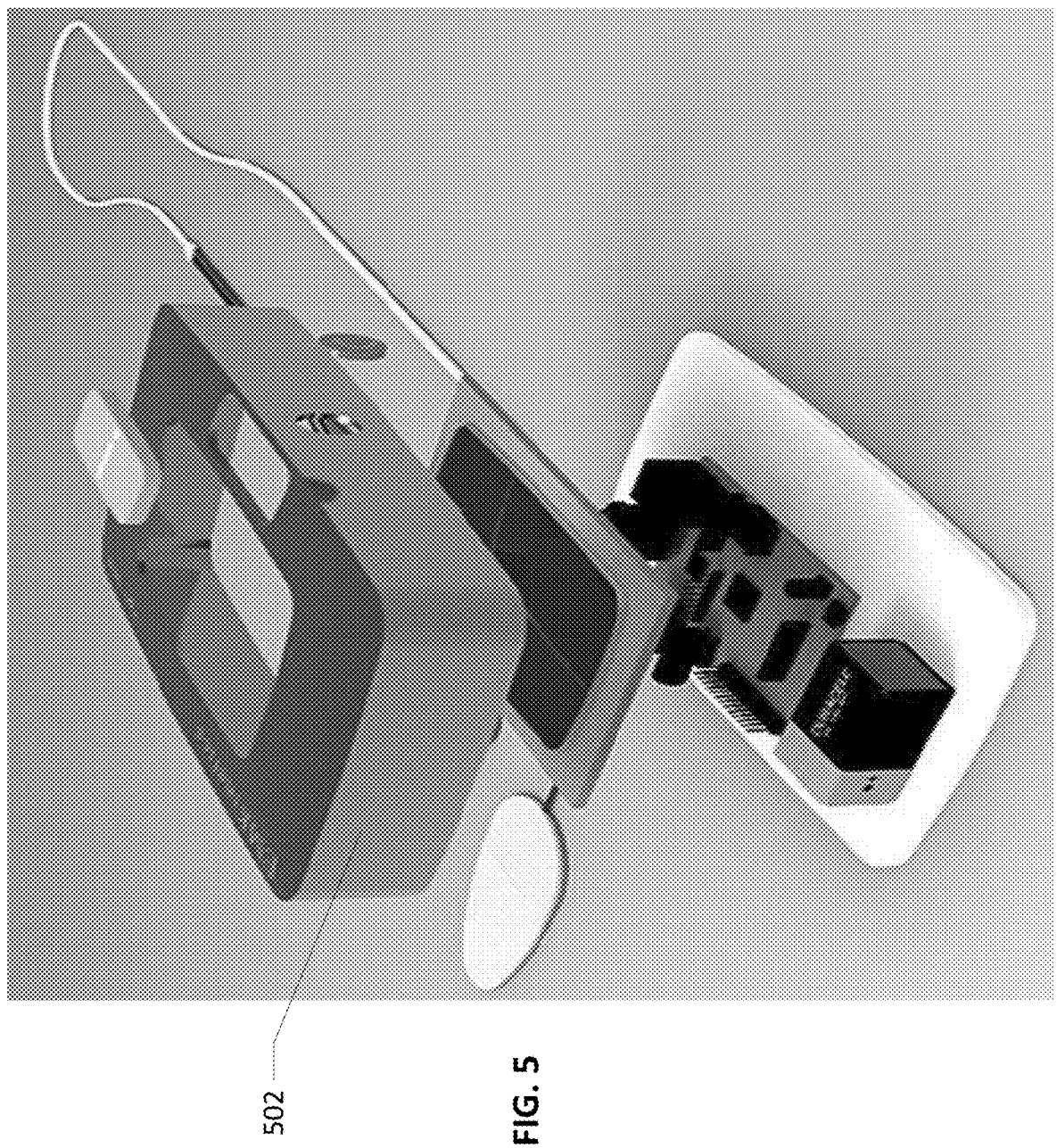
FIG. 5 shows an exploded view of the external generator or controller that can be used in some embodiments of the addiction treatment system.

FIG. 5 shows an exploded view of the external generator or controller that can be used in some embodiments of the addiction treatment system. The external generator/controller has housing 502 which contains internal components. The internal components may include a microprocessor, memory, a battery, on/off switches and various other electronic components for storing various operational and functional programs and executing those programs in accordance with a desired instruction set for the relevant indication or malady. Such programs will include but not be limited to instructions related to the parameters for electronic pulses which emit from the electrodes. They typical instruction set will include the desired pulse width, frequency, amplitude and the desired time intervals, and possibly, time length, for the therapy. The instructions may include more or less information as desired, such as burst modes, high frequency sequencing, coordinated reset functions and the like. In addition to delivering pulses, the generator/controller may also contain electronics for sensing F and M waves, and the ability to display, interpret and/or act on such sensed F and M waves. "Acting on" may mean that the controller analyzes and determines whether the parameter instruction set requires adjustments in order to maximize therapy effectiveness. If an adjustment is required, the instruction set will either make an automatic adjustment or send an alert or other information to the display to prompt a manual adjustment.

Figure 6:
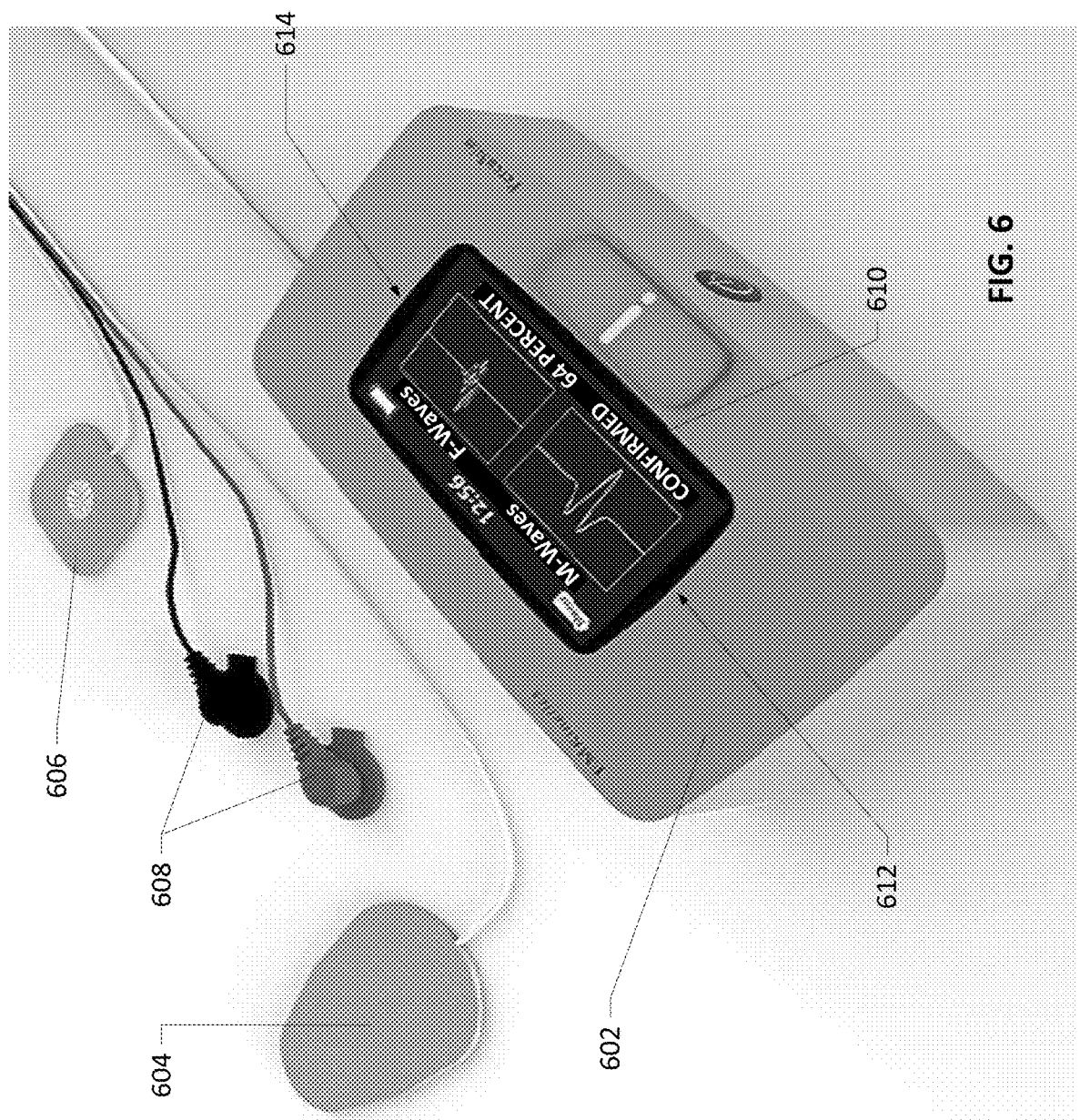
FIG. 6 shows the external generator/controller in FIG. 5.

FIG. 6 shows the external generator/controller in FIG. 5 in a non-exploded view with electrodes 604 and 606 and F/M wave sensors 608 all connected via insulated wires. The display 610 shown in this example displays an M-wave confirmation result 612 and an F-wave display 614 that shows the F-wave percent. The display may show other information such as the pulse parameters described above. In some embodiments, the external generator/controller provides a manual mode switch for determining which mode the system will be set to. It also contains an on/off switch and a display for displaying various information relating to the therapy and/or pulse parameters. The system may include two electrodes, one of which can be a stimulating electrode and one a return electrode. It should be understood, that any of the systems may contain two surface, or skin, electrodes or two percutaneous microneedle electrodes or one percutaneous electrode and one surface electrode. The electrodes may be similar to those disclosed herein, or to those already known in the art and currently sold on the market. This embodiment may also have one or more EMG sensing electrodes to sense F-Wave and M-Wave electrodes. All the electrodes may be connected to a generator/controller via a connection cable or wireless connection.

Figure 7:
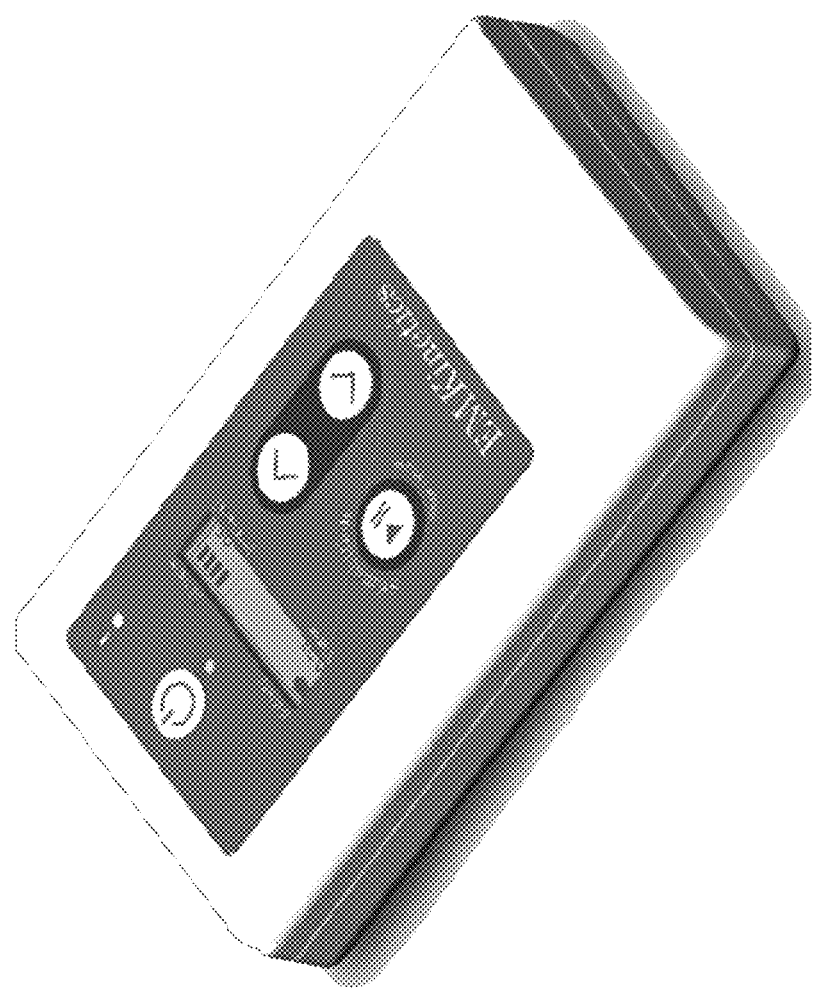
FIG. 7 shows another embodiment of a generator/controller.

FIG. 7 shows another embodiment of a generator/controller. This generator/controller can have all, some of, or additional attributes as those generator/controllers disclosed herein. FIG. 7 has the components in a compact, portable case. It may have advanced features, such as wireless communication, such as Bluetooth, or other wireless technology, and the ability to communicate with current smartphones or other computers via different applications. For example, any of the embodiments disclosed herein may include a controller which sends, and possible receives, data to/from a centralized server wirelessly. The connection may be via Wi-Fi, Bluetooth, cellular connection etc. The controller may be a smartphone, tablet, or other computer and/or may communicate with a smartphone, tablet, or other computer. The data sent from the controller and/or received by the controller may be anonymous or patient specific data. The data sent/received may be specific to one person or may be aggregate data of more than one user.

Alternatively, all or some of the functions of the generator/controller may be incorporated into a mobile computing device, such as a smart phone, tablet, mobile phone etc. The mobile computing device may include an "app" or application installed on the mobile device, which controls the functions of the electrodes, display and/or mobile device. The electrodes may be incorporated into the casing of the generator/controller, for example in a ball or handheld format. The electrodes may be incorporated into a casing which is physically attached to a mobile computing device. The casing may be powered by the mobile computing device or may be powered separately. Electrodes may be dry and built into the case for stimulation and EMG so that the user is in contact with the electrodes when the case is gripped. Electrodes may alternatively be wet and replaceable with attachments, such as snaps, which attach to, or connect to, the case. The app may use an EMG incorporated into the case, or may use accelerometers in the mobile device itself to measure intensity of stimulation. Since the gripping of the case may cause the fingers of the user to lay on the touchscreen display, the touchscreen may sense contraction of the fingers/hand and give an indication of stimulation presence/intensity. The touchscreen may sense the manner in which the fingers move (distance, direction, number of fingers etc.) or with 3D touch, the pressure on the screen may be measured.

The generator/controller and/or electrodes may also be incorporated into a glove, patch, band (wrist or arm or finger or hand), ring, etc.

Figure 8:
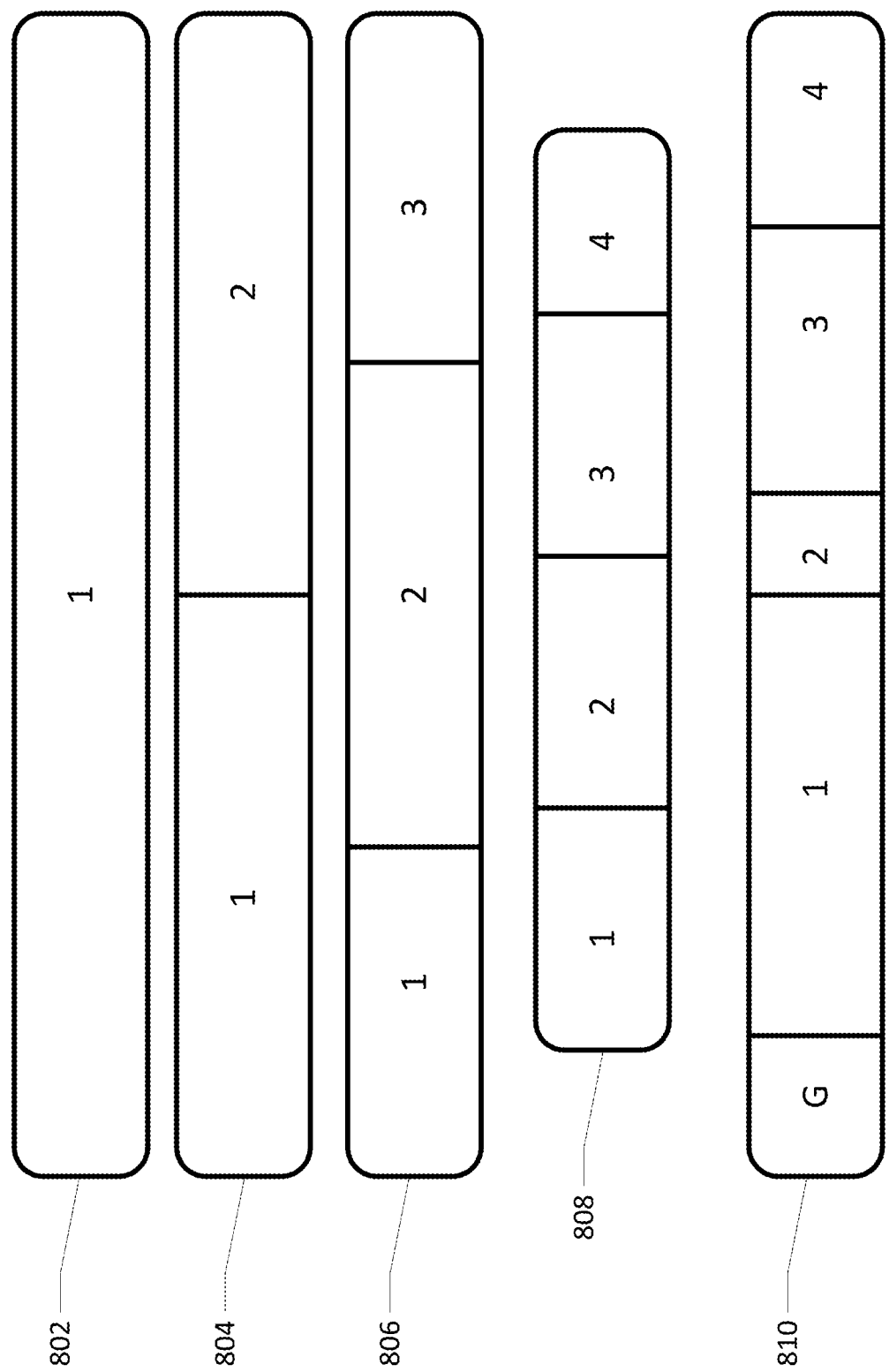
FIG. 8 shows four exemplary patch electrodes.

FIG. 8 shows four exemplary patch electrodes that are suitable to use with the addiction treatment system. Patch 802 is a patch electrode with only one surface electrode contact area, 1. Patch 804 is a patch electrode configuration where the patch contains 2 electrode contact areas, 1 and 2. Likewise, patch 806 includes 3 electrode contact areas, 1, 2 and 3. Patch 808 includes 4 contact areas, 1, 2, 3 and 4. Patch 810 includes 5 electrode contact areas, with one contact area, G, being configured to serve as a possible ground for the other electrodes, although any of the electrodes may serve as a ground electrode.

FIG. 8 shows a few of the different configurations of electrodes. These contact areas can be equally spaced or spaced according to the anatomy of the desired stimulation area. For example, in patch 808, contact area 4 may be the same size or smaller or larger than contact area 3 depending on the stimulation area desired. Additionally, FIG. 8 show patch electrodes, but it should be understood that the descriptions here are translatable to microneedle electrodes used alone or in conjunction with patch electrodes or fully implantable electrodes or both.

Figure 9:
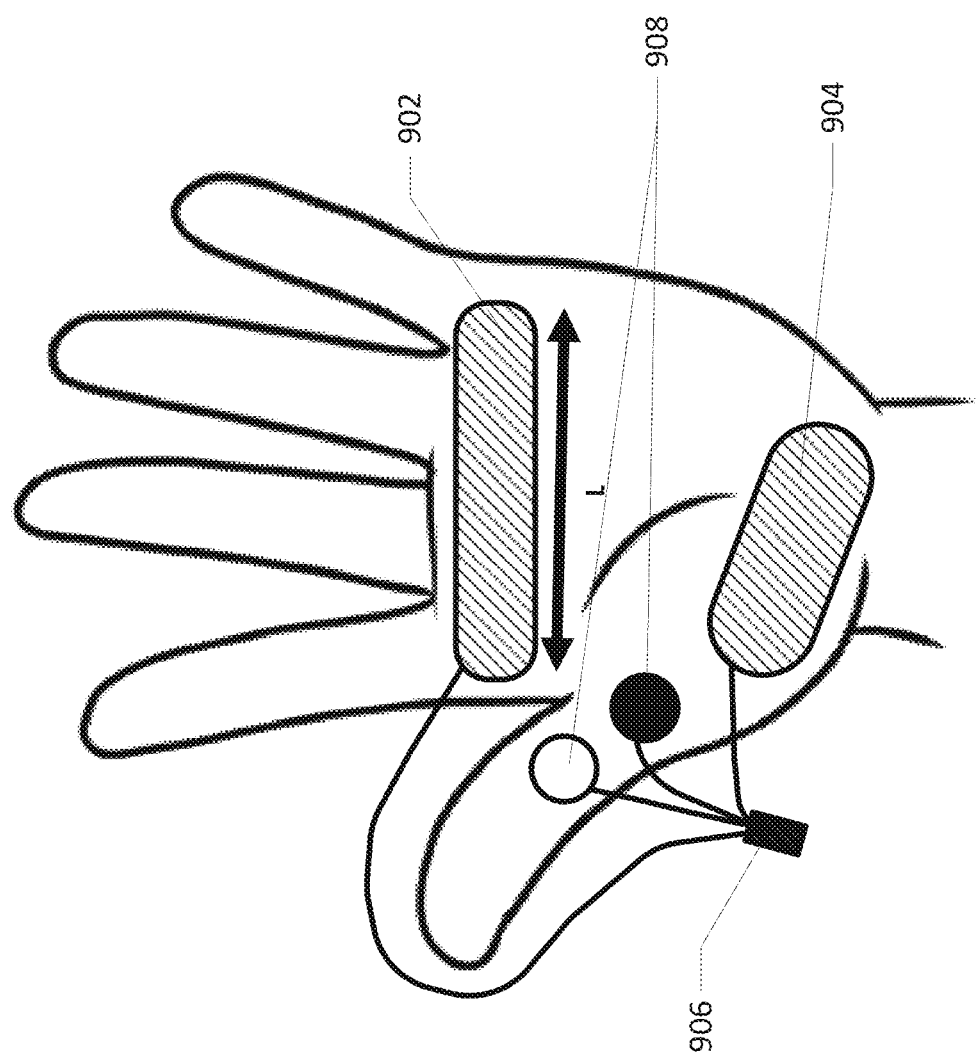
FIG. 9 shows electrodes designed for the palmar surface of the hands along with F/M wave detecting electrodes

FIG. 9 shows electrodes designed for the palmar surface of the hands along with F/M wave detecting electrodes 908. In FIG. 9, contact electrode(s) 902 are placed across the upper palm portion of the hand and second electrode 904 is place across towards, near or on the heel of the hand. The electrodes are connected to generator/controller 906 and electrical pulses are delivered to the hand per the instructions on the controller. Depending on the length "L" and placement of electrode 902, electrical stimulation of the hand will stimulate the Median or the Ulnar nerve or both. It should be understood that depending on the therapy and other considerations, the desired stimulation may be either one or both the Ulnar or Median nerve, bur for addiction, is preferably the Ulnar nerve. Detecting electrodes 908 may be placed in any appropriate location, including on the fingers, palm, thumb, back of hand, wrist, etc.

Although the electrodes shown here, and in other embodiments, may be shown on the palmar side of the hand, electrodes may be placed alternatively, or also on the dorsal side of the hand, where dorsal branches of the ulnar nerve can be stimulated.

Figure 10:
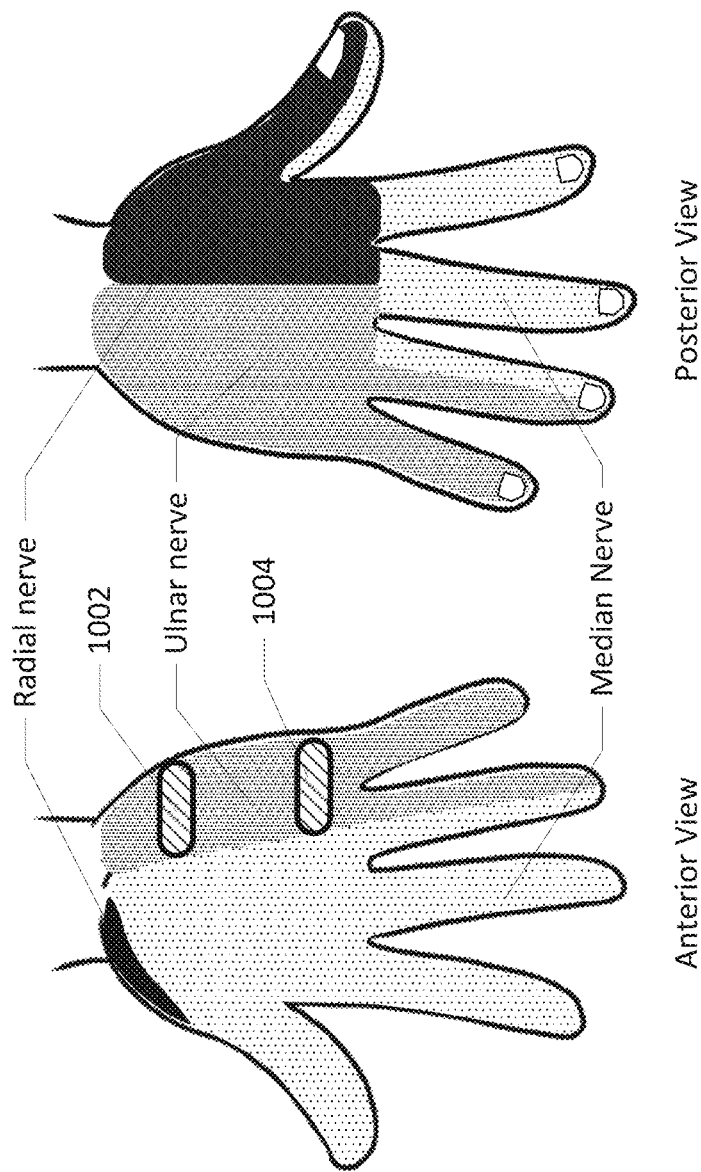
FIG. 10 shows placement of electrodes to preferentially or only stimulate the Ulnar nerves.
Figure 11:
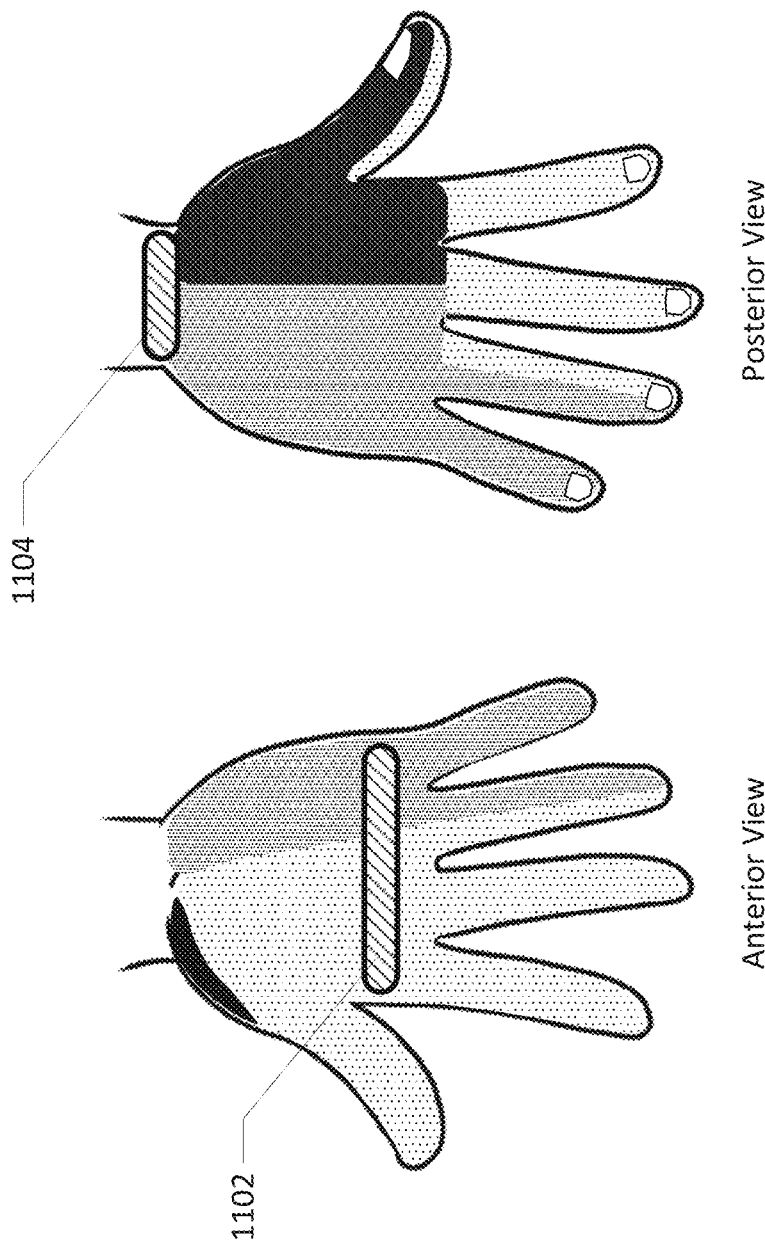
FIG. 11 shows electrodes placed on the posterior portion of the hand to stimulate both Ulnar and Median nerve simultaneously.

FIG. 10 shows placement of electrodes 1002 and 1004 to preferentially or only stimulate the Ulnar nerves. FIG. 11 shows electrode 1102 placed on the anterior and electrode 1104 placed on the posterior portion of the hand to stimulate both Ulnar and Median nerve simultaneously.

Figure 12:
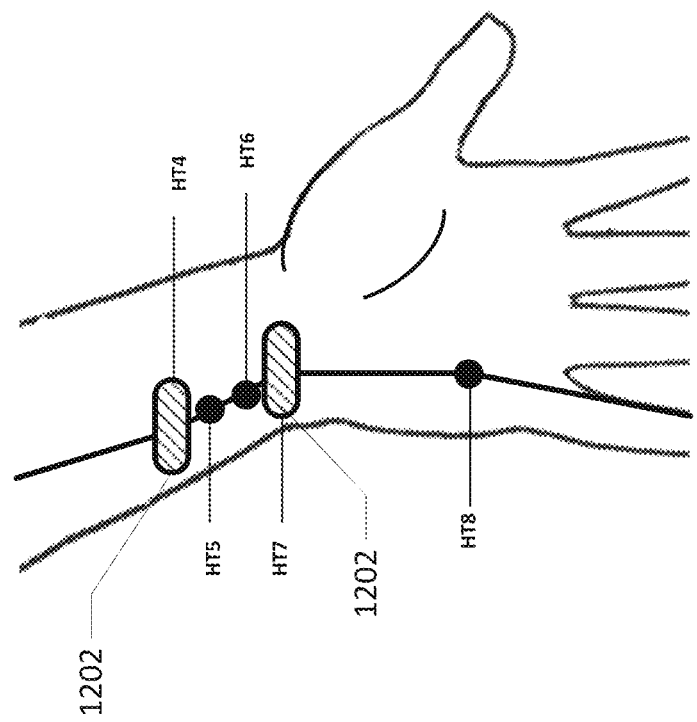
FIG. 12 shows an example where electrodes are placed on or near one or more of the HT acupuncture points.

FIG. 12 shows an example where electrodes are placed on or near one or more of the HT acupuncture points. In this example, electrodes 1202 are places on point HT4 and HT7 (shen men), but any one or more of the HT points may be used.

Figure 13:
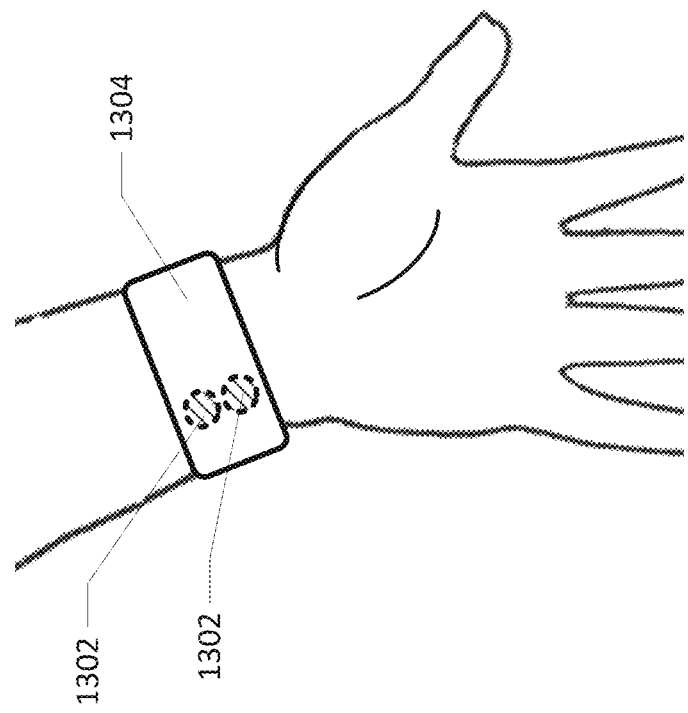
FIG. 13 shows an example where electrodes are placed on the underside of a band.

FIG. 13 shows an example where electrodes 1302 are placed on the underside of a band, such as wristband 1304, so that they are near the ulnar nerve, or a branch thereof, and/or near the HT acupuncture line to stimulate one or both of the ulnar nerve and HT line. Note that several embodiments disclosed herein show two electrodes, which may represent a stimulating and a ground electrode, but one, or more than 2 electrodes may be used. Also, any of the embodiments disclosed herein may include a sensor or sensors, whether or not a sensor is shown in the figures.

FIG. 14 shows electrodes 1402 incorporated into sleeve 1402 to stimulate one or both of the ulnar nerve and the HT line. Any of the wearable patches, sleeves, rings, bands, etc. may also incorporate the controller, or may incorporate wired or wireless communication with a separate controller, such as a smartphone or tablet. Preferably the stimulation device is wearable and portable, however, the device may be used only intermittently when the subject can sit/lie with the device, such as while sleeping or sitting.

FIG. 15 shows electrodes incorporated into wristband 1502 to stimulate one or both of the ulnar nerve and the HT line.

FIG. 16 shows electrodes incorporated into hand-band, glove, or fingerless glove 1602 to stimulate one or both of the ulnar nerve and the HT line.

Figure 17:
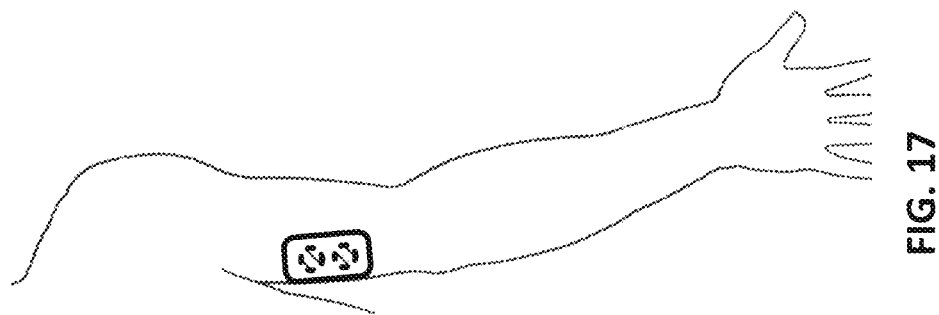
FIG. 17 shows electrodes incorporated into an arm patch.

FIG. 17 shows electrodes incorporated into an arm patch, which can be hidden underneath clothing.

Figure 18:
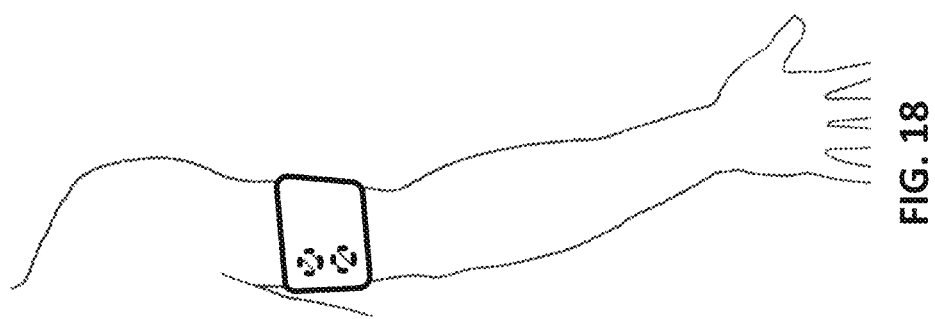
FIG. 18 shows electrodes incorporated into an arm band.

FIG. 18 shows electrodes incorporated into an arm band.

Figure 19:
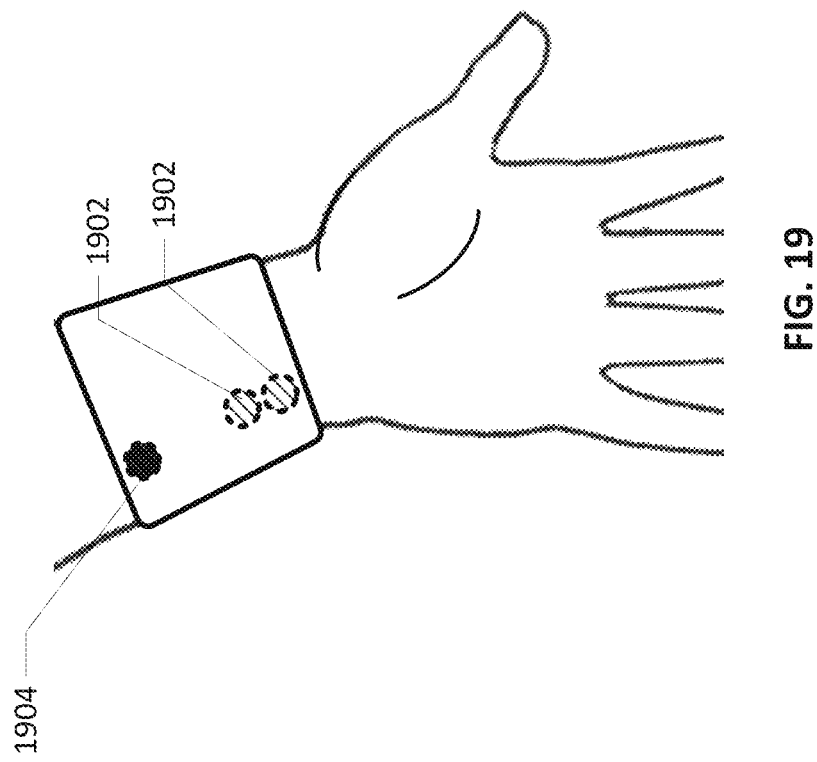
FIG. 19 shows electrodes and sensor incorporated into a wristband.

FIG. 19 shows electrodes 1902 incorporated into a wristband and also shows sensor 1604 incorporated into the band. The sensor or sensors may be placed anywhere where they will pick up F-waves and/or M-waves. Preferably, the sensor is at least about 0.5 cm to about 2 cm away from the stimulating or ground electrodes.

Figure 20:
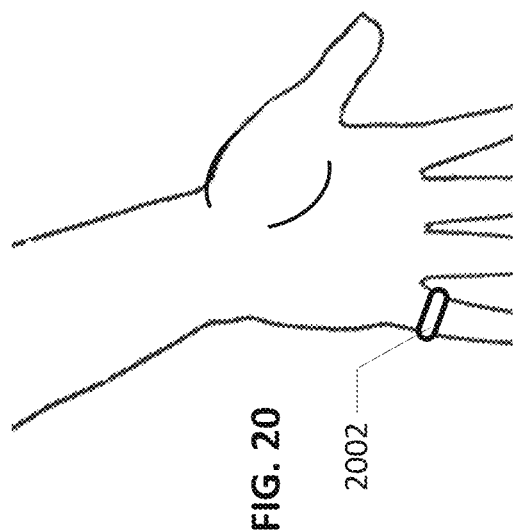
FIG. 20 shows a ring or finger band which incorporates the electrodes and optionally sensors.

FIG. 20 shows ring or finger band 2002 which incorporates the electrode(s) and optionally sensor(s).

Figure 21:
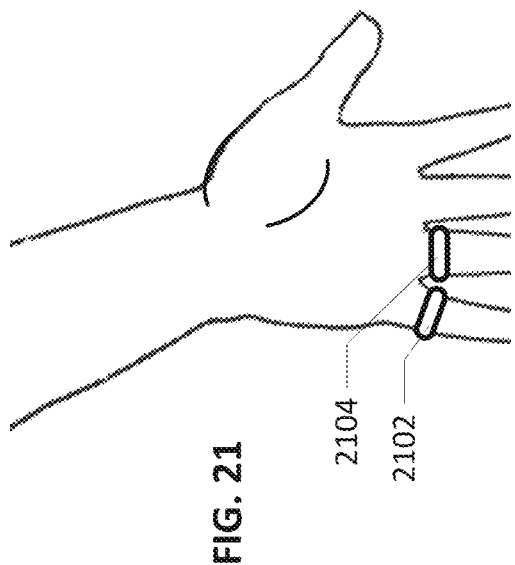
FIG. 21 shows two rings/finger bands which may incorporate sensors and/or electrodes.

FIG. 21 shows two rings/finger bands 2102 and 2104 which may incorporate sensors and/or electrodes. For example, each of the rings may incorporate one of two electrodes. Or, one ring may incorporate one or two electrodes and one ring may incorporate a sensor.

The figures are exemplary only. The addiction treatment system contemplates placing the electrode(s) in one or more of the combinations listed herein, or in other combinations, as required to achieve the desired stimulation therapy. Also, the addiction treatment system contemplates using single electrodes or one or more devices with two or more electrodes each that may stimulate with a more refined or focused field. For example, it is known in the art to use "anodal guarding" to localize the electric field to stimulate the desired areas while electrical "guarding" or reducing the field to not stimulate those other areas surrounding the particular focus of the stimulation therapy. Additionally, while not shown in all of the figures herein, the invention contemplates that sensing electrode(s) (as shown in FIG. 19) may be used in any of the embodiments. Several figures show transcutaneous electrodes, but it should be understood that the descriptions here are translatable to percutaneous electrodes used alone or in conjunction with transcutaneous electrodes or fully implantable electrodes or both.

The type of energy delivered to the nerve or nerves during stimulation by the device may depend on the pulse parameters. For example, in one therapy type, the pulse parameters have a frequency of somewhere between about 1-20 hz, a pulse width between about 0-500 microseconds and an amplitude of between about 0 and 90 mA. In another therapy, high frequency stimulation can be used, namely frequencies from about 20 hz up to about 10,000 hz. Such high frequencies can be effective using either external electrodes, or fully implantable electrodes, or both. The electrodes are placed in a location to stimulate the Ulnar nerve, the HT line nerve or both areas.

For example, in some embodiments, a user may receive a 30-minute treatment (15-minutes on each hand/wrist) (20 Hz treatment: pulse frequency of 20 Hz, pulse width of 200 μs, and a 50% duty cycle). Device current may be self-adjusted to the highest comfortable level via the controller using the sensors.

The energy pulse amplitude may also vary during the treatment. This modulation can increase both comfort and efficacy. For example, the pulse energy applied to the electrodes may be at 100% amplitude for X pulses (for example, 5 pulses) and then at a lower amplitude (for example, 50% amplitude) for Y pulses (for example, 5 pulses). The pulse amplitude and length may vary, for example, there may be two amplitude levels, or 3 or more. The different amplitude durations may be the same, or they may be different. The amplitude variations may be preset, or may be reset during the use of the device.

Figure 22:
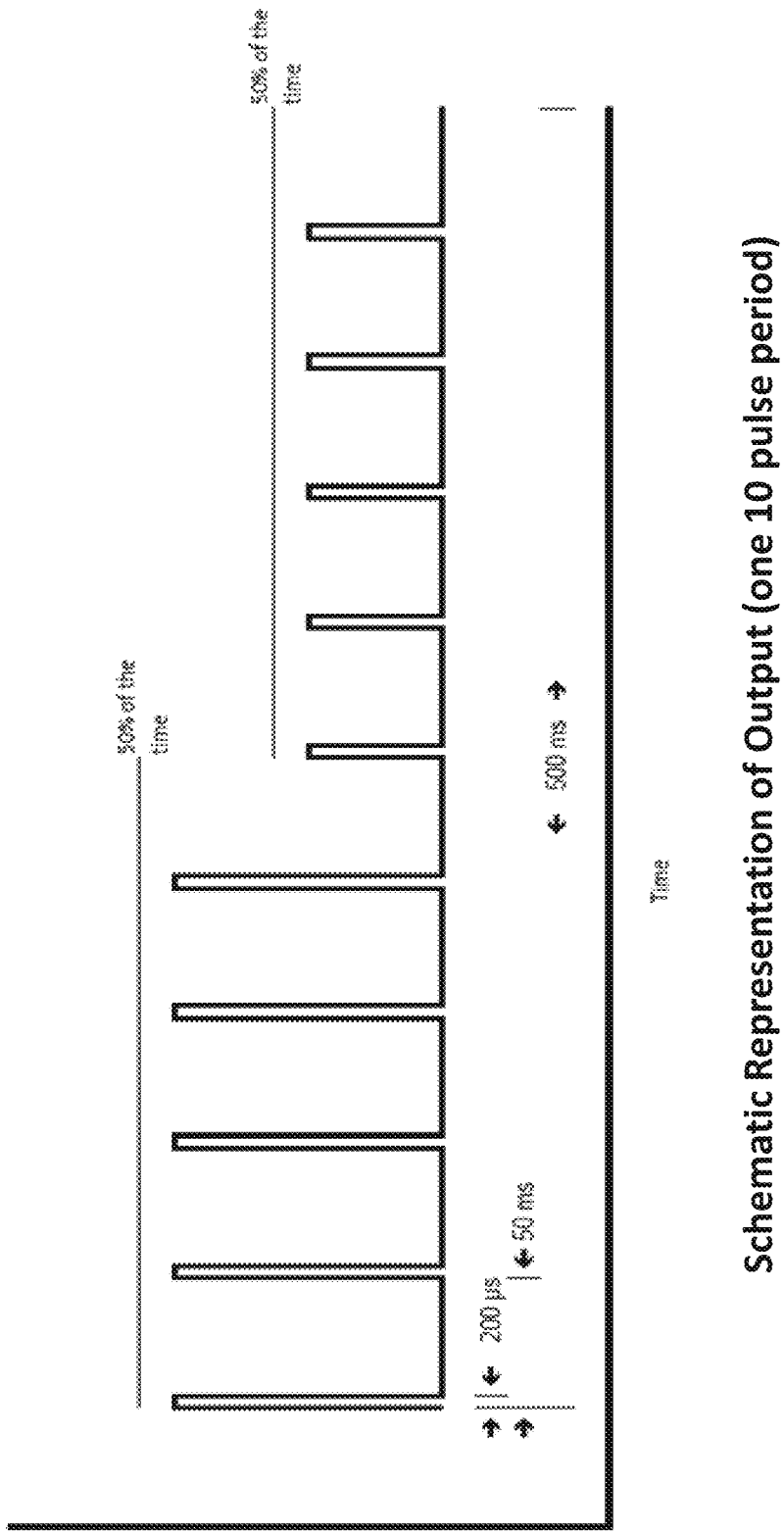
FIG. 22 shows a graph of varying amplitudes.

FIG. 22 shows one example of varying amplitudes where the amplitude magnitude is 100% and 50%, each for 5 pulses, alternating between 100% and 50% amplitude. More complicated variations are also envisioned. For example, the amplitude may vary in a sine function, or a multiple level function with the different amplitude lengths varying per amplitude. The amplitude variations may be the same across users or custom to each user, or even each user experience.

The parameters of the amplitude function include amplitude as a percent of maximum, amplitude time length, amplitude number of pulses, number of different amplitudes, order of different amplitudes, etc. These parameters may be communicated to a remote server for analysis to optimize treatment of individual users in the future. The data may also be aggregated (preferably anonymously) to develop treatment algorithms for different patient populations. Effectiveness input from the individual users may also be incorporated into the algorithms, for example pain level over time, comfort level, medication taken etc.

Similarly, pulse frequency parameters can also be modulated. Similarly, pulse width parameters an also be modulated.

In some embodiments of the device, an amplitude (and/or frequency) modulator adapter may be added to a commercially available TENS (Transcutaneous Electrical Nerve Stimulation) device. This adapter would modulate the amplitude and/or frequency of the signal produced by the TENS device so that the signal delivered to the user via the electrodes can be optimized for comfort and efficacy.

Some embodiments allow the user to use the device inconspicuously, for example at work, or in a meeting. The electrodes may be part of a phone case so that the user's hand is in contact with the electrodes while holding the phone. The electrodes may be part of a beverage mug, computer mouse, steering wheel, etc.

Principles of Electromyography

Figure 23:
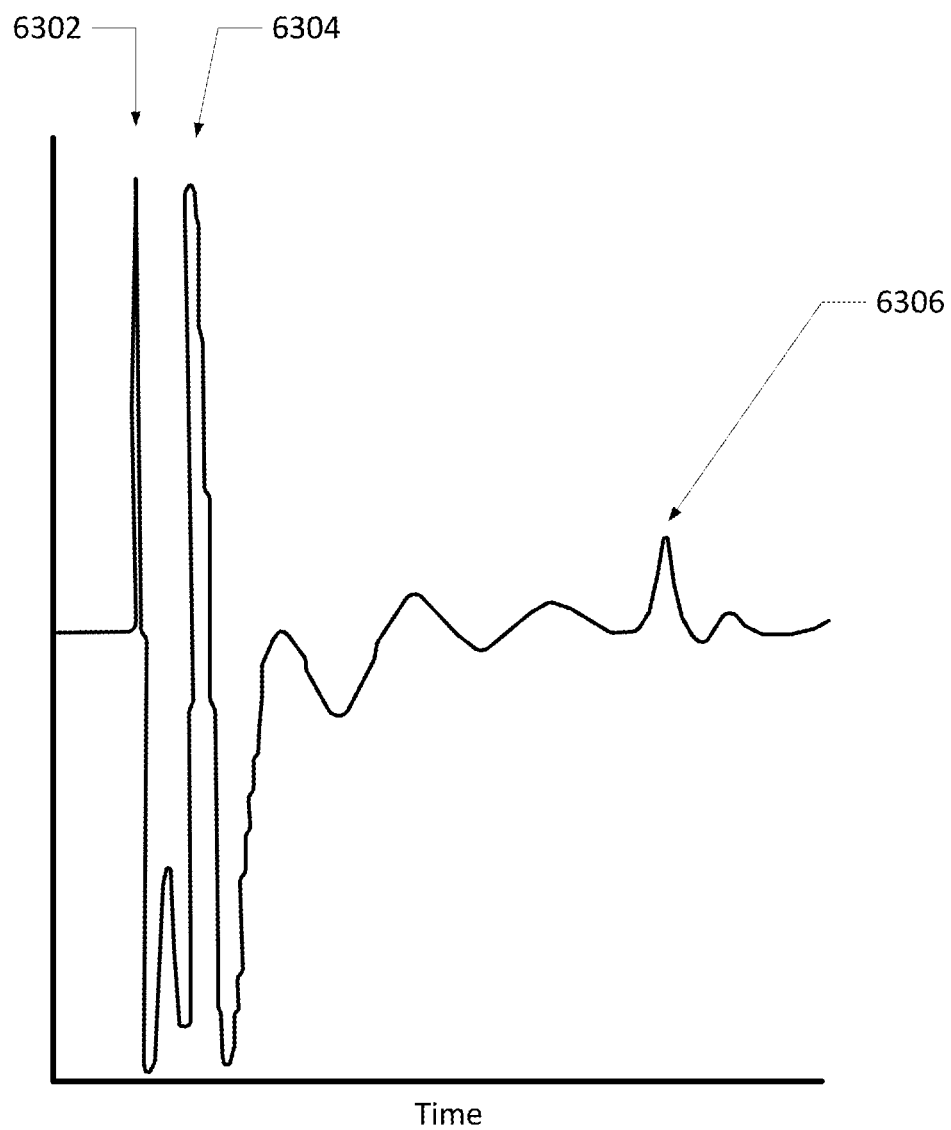
FIG. 23 shows a graph of detected voltage vs. time and shows an M-wave and F-wave following stimulation.

See FIG. 23 for the following discussion. The system also captures and displays electromyographic information during the treatment. Electromyography is the study of the electrical signals in the muscles for analysis of the behavior of the muscle or nervous systems in a body. During electrical neural muscle stimulation, signals called M-waves and F-waves are created by the body in the stimulated muscles and nerves in response to the electrical stimulation. In neuroscience, the M-Wave is the first, and the F-wave is the second, voltage change observed after electrical stimulation is applied to the distal region of a nerve. F-waves are often used to measure nerve conduction velocity, and are particularly useful for evaluating conduction problems in the proximal region of nerves (i.e., portions of nerves near the spinal cord). The signal is called the F-wave because it was initially recorded in the foot muscles.

In a typical F-wave study, a strong electrical stimulus (above maximal muscle stimulation levels) is applied to the skin surface above (proximally to) the distal portion of a nerve so that the impulse travels both distally (towards the muscle fiber) and proximally (back to the motor neurons of the spinal cord; these directions are also known as orthodromic and antidromic, respectively). When the orthodromic stimulus reaches the muscle fiber, it elicits a strong M-response indicative of muscle contraction (M-wave). When the antidromic stimulus reaches the motor neuron cell bodies, a small portion of the motor neurons fire in the other direction and an orthodromic wave travels back down the nerve towards the muscle. This reflected stimulus evokes a small proportion of the muscle fibers causing a small, second compound muscle action potential (CMAP) called the F-wave.

FIG. 23 shows a graph of detected voltage vs. time and shows M-wave 6304 and F-wave 6306 following stimulation 6302. This type of graph may be displayed by the controller to the end user. Alternatively, a different parameter of an M-wave and/or an F-wave may be displayed to the user, such as whether or not the wave exists, the amplitude of the wave, the travel time of the wave, etc.

The generator/controller may capture and display both the M-wave and F-wave on the display screen during confirmation and treatment modes. Being able to view the M-waves and F-waves during treatments allows the operator to confirm maximal stimulation of the nerve in question (Ulnar, Median or Tibial) and its branches in the feet; and the median and Ulnar nerves in the hand.

Example of Data Processing System

Figure 24:
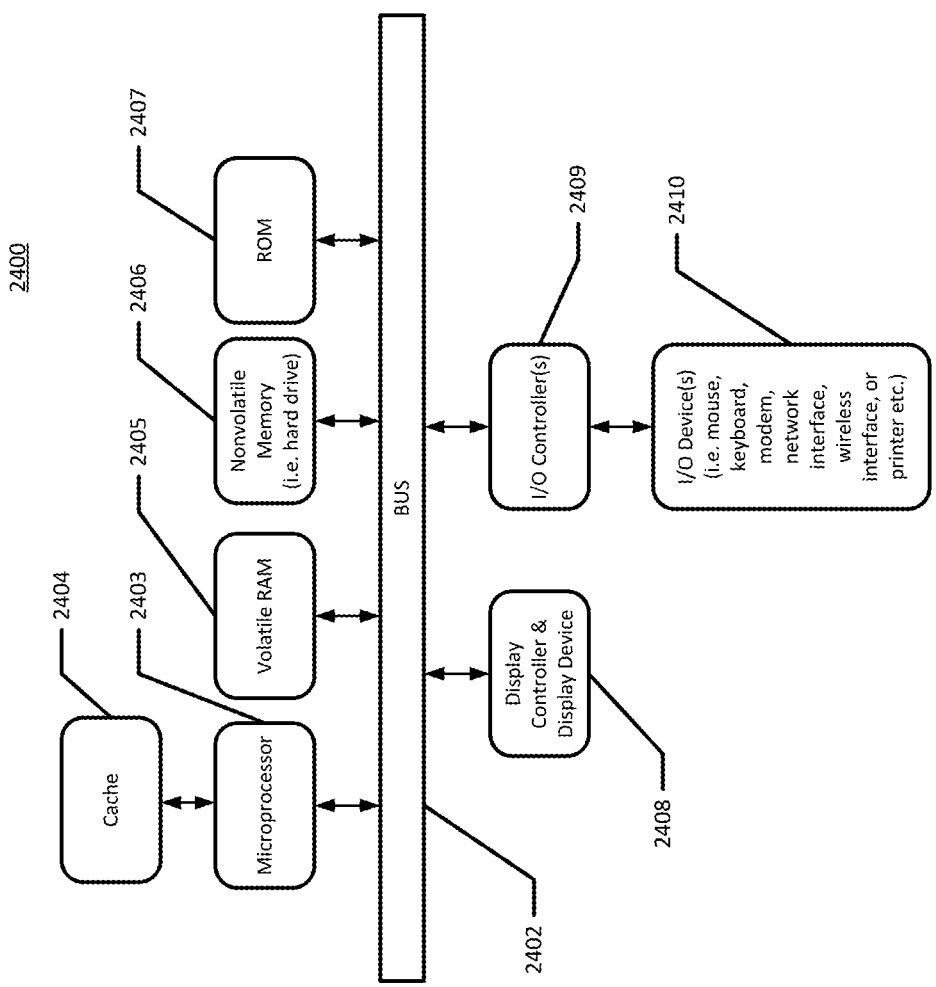
FIG. 24 is a block diagram of a data processing system.

FIG. 24 is a block diagram of a data processing system, which may be used with any embodiment of the invention. For example, the system 2400 may be used as part of a controller, server, mobile device, hand piece, computer, tablet, etc. Note that while FIG. 24 illustrates various components of a computer system, it is not intended to represent any particular architecture or manner of interconnecting the components; as such details are not germane to the addiction treatment system. It will also be appreciated that network computers, handheld computers, mobile devices, tablets, cell phones and other data processing systems which have fewer components or perhaps more components may also be used with the addiction treatment system.

As shown in FIG. 24, the computer system 2400, which is a form of a data processing system, includes a bus or interconnect 2402 which is coupled to one or more microprocessors 2403 and a ROM 2407, a volatile RAM 2405, and a non-volatile memory 2406. The microprocessor 2403 is coupled to cache memory 2404. The bus 2402 interconnects these various components together and also interconnects these components 2403, 2407, 2405, and 2406 to a display controller and display device 2408, as well as to input/output (I/O) devices 2410, which may be mice, keyboards, modems, network interfaces, printers, and other devices which are well-known in the art.

Typically, the input/output devices 2410 are coupled to the system through input/output controllers 2409. The volatile RAM 2405 is typically implemented as dynamic RAM (DRAM) which requires power continuously in order to refresh or maintain the data in the memory. The non-volatile memory 2406 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 24 shows that the non-volatile memory is a local device coupled directly to the rest of the components in the data processing system, the addiction treatment system may utilize a non-volatile memory which is remote from the system; such as, a network storage device which is coupled to the data processing system through a network interface such as a modem or Ethernet interface. The bus 2402 may include one or more buses connected to each other through various bridges, controllers, and/or adapters, as is well-known in the art. In one embodiment, the I/O controller 2409 includes a USB (Universal Serial Bus) adapter for controlling USB peripherals. Alternatively, I/O controller 2409 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the FIGS. can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the FIGS. herein may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Figure 25B:
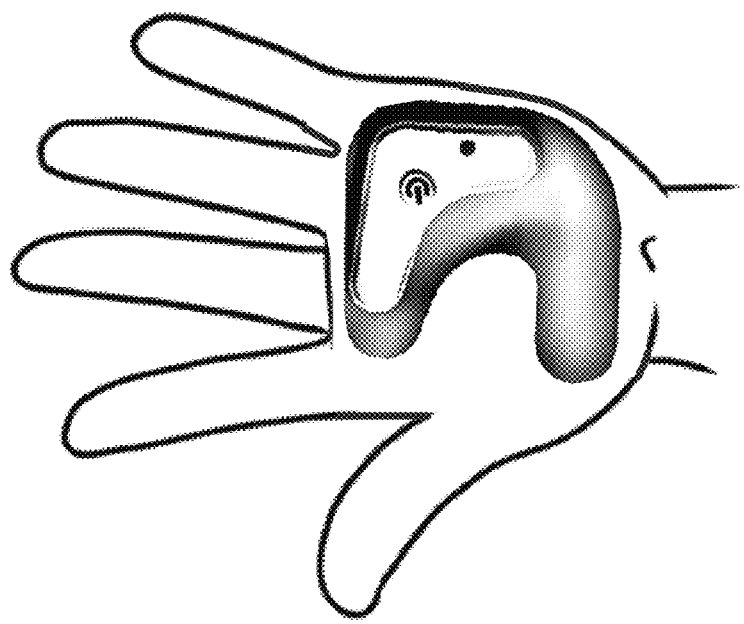
FIGS. 25A and 25B show an embodiment which includes the controller in a single ergonomic package.
Figure 25A:
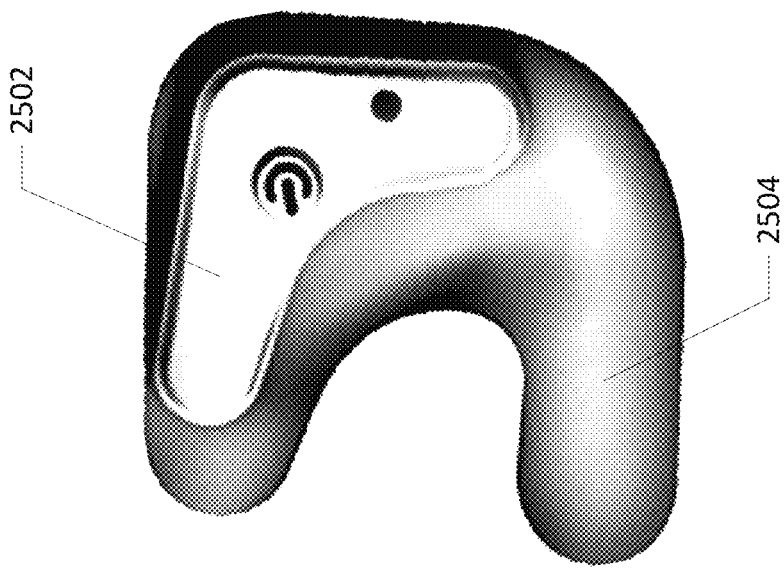

FIGS. 25A and 25B show an embodiment where the controller and electrodes are in a single ergonomic package. The package may include sensors as well. The device includes controller 2502 and flexible base 2504 as shown in FIG. 25A. The electrodes (not shown here) are integrated with, or connected to, the underside of the flexible base. The electrodes may be disposable and able to be disconnected and replaced for each use. Sensors may be incorporated into the palm side of the flexible base also. The base may be made from silicone or other appropriate material. FIG. 25B shows the device of FIG. 25A on a palm. The electrodes may be in contact with the area of the hand which is supplied by the ulnar nerve. Some embodiments may include an ergonomic package which has no visible wires.

Some embodiments of the addiction treatment system may include the application of heat and/or cold to the user. The application may be alternating between heat and cold. The application may be in addition to the treatment via electrodes, or may be an alternative to the electrode treatment. The hot/cold treatment may be via the same device surface as the electrodes, or may be via a different device/skin interface. The application of heat/cold may be in the same location as the electrode treatment, or may be at a different body location.

Some embodiments may include the ability to sense withdrawal/craving symptoms and/or addictive behavior and may be able to initiate treatment, or modify treatment as a result of the sensed symptoms/behavior. For example, the device may sense sweating using impedance sensors on the skin, which is a symptom of withdrawal. The impedance sensors may be the same electrodes as the treatment electrodes or may be a separate sensor, such as separate electrodes. As a result, the device may initiate a treatment cycle, or increase the frequency and/or intensity of the treatment. The change in treatment may be manual or automatic.

Other example of sensing withdrawal/craving symptoms or addictive behavior include sensing shaking or tremors via an accelerometer, sensing the heartbeat, heart rate or other heart parameter via the treatment electrodes, or other electrodes, sensing blood pressure or heart rate using a pressure sensor, chemical sensors sensing skin/sweat/breath/blood, sensing the ECG via the treatment electrodes of other electrodes, etc. Sensors may be on the skin or elsewhere. Some sensors may be implanted.

Some embodiments may include the ability to sense addictive behavior via connectivity to phones or other electronic devices. For example, the addiction treatment device may connect with phone apps (for example gambling apps) or other phone/electronic device info. The addiction treatment device may monitor certain physical motions, such as a motion associated with playing cards, or gambling, or using a particular electronic application. Or the device may monitor a particular motion associated with withdrawal/craving symptoms or addictive/use behavior, such as drinking, injecting, slurring speech, unstable walking, nodding, pupil dilation, slow reactions, etc. This may be done via accelerometers, cameras or other sensors.

In some embodiments, the device may connect with a global positioning system of a mobile electronic device to sense when the user is at particular locations, including flagged locations such as liquor stores, bars, meth clinics, high drug dealing locations, crack houses, etc.

Sensing, of addictive behavior and/or withdrawal/craving symptoms may be done on demand, on a scheduled basis, or randomly with or without the user's intervention. The sensing, for example, may be done as a random periodic check on the user.

Some embodiments of the addiction treatment system may include the ability to communicate compliance information, based on withdrawal/craving and/or addictive behavior sensors, to another party. The other party may be a family member or physician or other entity/person. This communication may be direct or via a remote server.

Some embodiments may include required compliance components, such as a locked wristband with mandatory treatment and/or mandatory sensing of compliance via withdrawal/craving symptom and/or addictive behavior sensors.

Some embodiments of the device are disguised so that they are not readily identified by others in public. For example, the device may be disguised as a watch, or a ring, or glove, or the device may be very small and on the inside of the wrist/hand.

In some embodiments, the device may delivery a punishment or reward based on the sensed addictive behavior and/or withdrawal/craving symptoms. For example, if the sensor senses that the user is participating in addictive behavior, the device may deliver an electric shock, an offensive and/or loud sound, or other undesirable sensation or alert. The device may include an interface (or a connection to an electronic device with an interface) which gives positive enforcement for good behavior. For example, the interface may display a "good job" or other encouragement if the user has avoided addictive behavior for a period of time, or if the user is needing the device less often or using a lower treatment intensity over time.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the addiction treatment system.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the addiction treatment system (in which case what is present herein shall prevail). The referenced items are provided solely for their disclosure prior to the filing date of the present application. Nothing herein is to be construed as an admission that the addiction treatment system is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the addiction treatment system is limited only by the appended claims.

What is claimed is:

1. An apparatus for mitigating addictive behavior, comprising:
    at least two electrodes for positioning in proximity to an ulnar nerve of a body of a subject;
    one or more sensors configured to detect physiologic parameters which correlate to one or more symptoms indicative of withdrawal from an addictive behavior of the subject; and
    a pulse generator programmed to receive a sensor output based on the detected physiologic parameters and to apply a treatment stimulation to the ulnar nerve through a skin surface of the subject such that the addictive behavior of the subject is reduced, wherein the pulse generator is configured to generate pulses of one or more different magnitudes, frequencies and/or durations, and wherein the treatment stimulation comprises electrical stimulation sufficient to produce F-waves which are detectable from the subject.

2. The apparatus of claim 1 wherein the treatment stimulation is applied automatically based on the sensor output.

3. The apparatus of claim 1 wherein the treatment stimulation is applied manually based on the sensor output.

4. The apparatus of claim 1 wherein the treatment stimulation is adjustable in treatment magnitude.

5. The apparatus of claim 1 wherein the treatment stimulation is adjustable in treatment frequency.

6. The apparatus of claim 1 wherein the treatment stimulation is adjustable in treatment duration.

7. The apparatus of claim 1 wherein one of the at least two electrodes is configured for placement upon a wrist of the subject.

8. The apparatus of claim 1 wherein one of the at least two electrodes is configured for placement upon an arm of the subject.

9. The apparatus of claim 1 wherein one of the at least two electrodes is configured for placement upon a hand of the subject.

10. The apparatus of claim 1 wherein the one or more sensors is configured to detect for a presence of sweat of the subject.

11. The apparatus of claim 1 wherein the one or more sensors is configured to detect for shaking or tremors of the subject.

12. The apparatus of claim 1 wherein the one or more sensors is configured to detect for a blood pressure level of the subject.

13. The apparatus of claim 1 wherein the one or more sensors is configured to detect for a dehydration level of the subject.

14. The apparatus of claim 1 wherein the one or more sensors is configured to detect for an impedance level from the skin of the subject.

15. The apparatus of claim 1 wherein the one or more sensors comprise an accelerometer.

16. The apparatus of claim 1 wherein the one or more sensors comprise a pressure sensor.

17. The apparatus of claim 1 wherein the one or more sensors is configured to detect for a substance correlated to the addictive behavior.

18. The apparatus of claim 1 wherein the addictive behavior comprises an activity.

19. The apparatus of claim 18 wherein the addictive behavior comprises electronic device overuse.

20. The apparatus of claim 1 wherein the physiologic parameters which correlate to the one or more symptoms comprise shaking or tremors, changes in heart rate, blood pressure, or sweating.

21. The apparatus of claim 1 wherein the treatment stimulation is applied at a frequency interval ranging over 0 to 100 minutes or greater.

22. The apparatus of claim 1 wherein the treatment stimulation is applied at a frequency of 5 Hz to 20 Hz.

23. The apparatus of claim 22 wherein the treatment stimulation is applied in a train of 5 pulses or up to 10 pulses.

24. The apparatus of claim 1 wherein the pulse generator is adjustable based on F-waves, M-waves, or H-reflex detected from the body.

25. The apparatus of claim 1 further comprising an interface in communication with the pulse generator, wherein the interface is configured to provide positive enforcement to the subject for a reduction in the addictive behavior.

26. A method for mitigating addictive behavior, comprising:
  detecting one or more physiologic parameters via one or more sensors correlating to one or more symptoms indicative of withdrawal from an addictive behavior of a subject;
  determining a treatment stimulation based on the sensor output from the detected physiologic parameters;
  applying the treatment stimulation via at least two electrodes to an ulnar nerve through a skin surface of the subject via a pulse generator such that the addictive behavior of the subject is reduced, wherein the pulse generator is configured to generate pulses of one or more different magnitudes, frequencies and/or durations; and
  adjusting the pulse generator based on F-waves, M-waves, or H-reflex detected from the body.

27. The method of claim 26 wherein applying the treatment stimulation comprises automatically applying the treatment stimulation.

28. The method of claim 26 wherein applying the treatment stimulation comprises manually applying the treatment stimulation.

29. The method of claim 26 wherein applying the treatment stimulation comprises adjusting a treatment magnitude of the treatment stimulation.

30. The method of claim 26 wherein applying the treatment stimulation comprises adjusting a treatment frequency of the treatment stimulation.

31. The method of claim 26 wherein applying the treatment stimulation comprises adjusting a treatment duration of the treatment stimulation.

32. The method of claim 26 wherein applying the treatment stimulation comprises applying the treatment stimulation through a wrist of the subject.

33. The method of claim 26 wherein applying the treatment stimulation comprises applying the treatment stimulation through an arm of the subject.

34. The method of claim 26 wherein applying the treatment stimulation comprises applying the treatment stimulation through a hand of the subject.

35. The method of claim 26 wherein detecting one or more physiologic parameters comprises detecting for a presence of sweat of the subject.

36. The method of claim 26 wherein detecting one or more physiologic parameters comprises detecting for shaking or tremors of the subject.

37. The method of claim 26 wherein detecting one or more physiologic parameters comprises detecting a blood pressure level of the subject.

38. The method of claim 26 wherein detecting one or more physiologic parameters comprises detecting a dehydration level of the subject.

39. The method of claim 26 wherein detecting one or more physiologic parameters comprises detecting an impedance level from the skin of the subject.

40. The method of claim 26 wherein the one or more sensors comprise an accelerometer.

41. The method of claim 26 wherein the one or more sensors comprise a pressure sensor.

42. The method of claim 26 wherein the one or more sensors is configured to detect for a substance correlated to the addictive behavior.

43. The method of claim 26 wherein the addictive behavior comprises electronic device overuse.

44. The method of claim 26 wherein detecting one or more physiologic parameters comprises detecting for shaking or tremors, changes in heart rate, blood pressure, and sweating.

45. The method of claim 26 wherein applying the treatment stimulation comprises applying an electrical stimulation sufficient to produce F-waves which are detectable from the subject.

46. The method of claim 26 wherein applying the treatment stimulation comprises applying the treatment stimulation at a frequency interval ranging over 0 to 100 minutes or greater.

47. The method of claim 26 wherein applying the treatment stimulation comprises applying the treatment stimulation at a frequency of 5 Hz to 20 Hz.

48. The method of claim 47 further comprising applying the treatment stimulation in a train of 5 pulses or up to 10 pulses.

49. The method of claim 26 further comprising displaying positive enforcement to the subject for a reduction in the addictive behavior.

50. An apparatus for mitigating addictive behavior, comprising:
  at least two electrodes for positioning in proximity to an ulnar nerve of a body of a subject;
  one or more sensors configured to detect physiologic parameters which correlate to one or more symptoms indicative of withdrawal from an addictive behavior comprising electronic device overuse of the subject; and
  a pulse generator programmed to receive a sensor output based on the detected physiologic parameters and to apply a treatment stimulation to the ulnar nerve through a skin surface of the subject such that the addictive behavior of the subject is reduced, wherein the pulse generator is configured to generate pulses of one or more different magnitudes, frequencies and/or durations.

51. An apparatus for mitigating addictive behavior, comprising:
  at least two electrodes for positioning in proximity to an ulnar nerve of a body of a subject;
  one or more sensors configured to detect physiologic parameters which correlate to one or more symptoms indicative of withdrawal from an addictive behavior of the subject; and
  a pulse generator programmed to receive a sensor output based on the detected physiologic parameters and to apply a treatment stimulation to the ulnar nerve through a skin surface of the subject such that the addictive behavior of the subject is reduced, wherein the pulse generator is configured to generate pulses of one or more different magnitudes, frequencies and/or durations, and wherein the pulse generator is adjustable based on F-waves, M-waves, or H-reflex detected from the body.

52. A method for mitigating addictive behavior, comprising:

detecting one or more physiologic parameters via one or more sensors correlating to one or more symptoms indicative of withdrawal from an addictive behavior comprised of electronic device overuse of a subject;

determining a treatment stimulation based on the sensor output from the detected physiologic parameters; and applying the treatment stimulation via at least two electrodes to an ulnar nerve through a skin surface of the subject via a pulse generator such that the addictive behavior of the subject is reduced, wherein the pulse generator is configured to generate pulses of one or more different magnitudes, frequencies and/or durations.

* * * * *